United States Patent [19]

Letzt et al.

[11] Patent Number: 5,612,869
[45] Date of Patent: Mar. 18, 1997

[54] ELECTRONIC HEALTH CARE COMPLIANCE ASSISTANCE

[75] Inventors: Alan M. Letzt, Burke, Va.; Lester M. Spandorfer, Cheltenham, Pa.

[73] Assignee: Innovative Enterprises International Corporation, Burke, Va.

[21] Appl. No.: 184,369

[22] Filed: Jan. 21, 1994

[51] Int. Cl.⁶ .................................................. G06F 159/00
[52] U.S. Cl. .......................... 395/203; 395/2.6; 395/2.92; 395/2.95
[58] Field of Search .......................... 364/413.01, 413.02; 368/10, 41, 107–109; 360/148, 309.4, 309.15; 221/2, 15; 381/36, 43; 395/2.4, 2.7, 2.8, 2.83, 2.1

[56] References Cited

U.S. PATENT DOCUMENTS

| | | | |
|---|---|---|---|
| 4,060,848 | 11/1977 | Hyatt | 364/200 |
| 4,223,801 | 9/1980 | Carlson | 221/3 |
| 4,258,354 | 3/1981 | Carmon et al. | 340/309.4 |
| 4,302,752 | 11/1981 | Weitzler | 340/309.4 |
| 4,419,016 | 12/1983 | Zoltan | 368/10 |
| 4,449,829 | 5/1984 | Ikemoto et al. | 368/63 |
| 4,504,153 | 3/1985 | Schollmeyer et al. | 368/10 |
| 4,588,303 | 5/1986 | Wirtschafter et al. | 368/10 |
| 4,682,299 | 7/1987 | McIntosh et al. | 340/309.4 |
| 4,695,954 | 9/1987 | Rose et al. | 364/479.06 |
| 4,725,997 | 2/1988 | Urquhart et al. | 368/10 |
| 4,731,765 | 3/1988 | Cole et al. | 368/10 |
| 4,768,176 | 8/1988 | Kehr et al. | 368/10 |
| 4,768,177 | 8/1988 | Kehr et al. | 368/10 |
| 4,831,562 | 5/1989 | McIntosh et al. | 340/309.15 |
| 4,837,719 | 6/1989 | McIntosh et al. | 340/309.15 |
| 4,926,572 | 5/1990 | Holmes | 368/10 |
| 4,942,544 | 7/1990 | McIntosh et al. | 340/309.15 |
| 4,962,491 | 10/1990 | Schaeffer | 368/21 |
| 4,970,662 | 11/1990 | Tanaka et al. | 364/250 |
| 5,088,056 | 2/1992 | McIntosh et al. | 364/413.02 |
| 5,099,463 | 3/1992 | Lloyd et al. | 368/10 |
| 5,148,944 | 9/1992 | Kaufman et al. | 221/131 |
| 5,157,640 | 10/1992 | Backner | 368/41 |
| 5,200,891 | 4/1993 | Kehr et al. | 364/413.01 |
| 5,357,427 | 10/1994 | Langen et al. | 364/443.02 |

FOREIGN PATENT DOCUMENTS

| | | |
|---|---|---|
| 0342859 | 11/1989 | European Pat. Off. . |
| 0526166 | 2/1993 | European Pat. Off. . |
| WO91/05311 | 4/1991 | WIPO . |
| WO94/06088 | 3/1994 | WIPO . |

*Primary Examiner*—Gail O. Hayes
*Assistant Examiner*—Frantzy Poinvil
*Attorney, Agent, or Firm*—Lowe, Price, LeBlanc & Becker

[57] ABSTRACT

An electronic health care compliance assistance system includes a user device and a host station used by a health care provider. The user device generates voice messages to remind a user when and how to take or refill prescribed medications, to attend to other health matters, and to keep doctors' appointments. Compressed digital speech is used to generate clear and natural sounding voice messages. A health care provider uses the host station to compose messages and to store a database of speech messages and related data. Data are transferred from the host station to the user device to generate a regimen that is customized for the user. A queuing system is provided for messages relating to medications having common dosing times. A parameter is defined to permit adaptive rescheduling of messages when a user does not respond. The user device provides adaptive and interactive audible and visual prompts to alert the user when one or more messages are ready to be played. A satellite device may be used to generate such prompts to alert the user to consult the user device for the message. User operated keys are provided to play a message, to repeat the message, to confirm that the desired action has been attended to, or to play a counseling message. The user device stores data on each user action and inaction, for transfer to the host station which compiles the data in a report for health care providers.

47 Claims, 10 Drawing Sheets

T4: TIME PERIOD WITHIN WHICH CNR REPEATS OF COUNSELING MESSAGE ARE ALLOWED.

CNR: LIMIT ON NUMBER OF REPEATS OF COUNSELING MESSAGE WITIN T4 TIME PERIOD

ELECTRONIC HEALTH CARE COMPLIANCE ASSISTANCE

TECHNICAL FIELD

This invention relates generally to prompting devices, and more particularly to devices for prompting a user to take a medication, or to perform other health care related actions, at or sufficiently close to prescribed times. Still more particularly, the invention relates to devices of the aforementioned type which provide detailed instructions to the user, which are programmable by a health care provider rather than the user, and which have a number of features as follows. The device according to the invention uses high performance compressed digital speech in order to generate clear and natural sounding voice messages which are more easily communicated, more flexible, and more memorable than messages communicated through synthetic speech, visual displays and alarms. Such a device is moreover adaptive to a particular user by changing the regimen messages in accordance with user compliance or non-compliance, and produces a record of the user's operation of the device relative to the device's prompts, messages, and normal operation.

BACKGROUND ART

Prescription medications are effective remedies for many patients when taken according to instructions. However, studies have shown that, on average, about 50% of patients do not comply with the prescribed medication regimens. A low rate of compliance with medication regimens results in a large number of hospitalizations and admissions to nursing homes every year. Consequently, various methods and apparatus have been made available to improve patient compliance with prescribed regimens in efforts to improve patient health.

There are many complex reasons why patients do not comply with their medication regimens. However, one major reason relates to memory. A large number of persons who take medications, particularly those over 65 years of age, fail to comply with a prescribed regimen because of one or more of the following: (1) forgetting to take a medication, (2) forgetting to take a medication at the correct time, (3) forgetting the correct dosage, (4) forgetting important warnings and instructions that accompany the medications, (5) forgetting to refill a prescription, (6) forgetting to perform a health-related activity such as a therapeutic exercise or pulse reading, or (7) forgetting to attend their next doctor's appointment.

There is thus a need in the prior art for improved methods and apparatus for assisting a patient's memory with respect to timing, dosage, and counseling information relating to prescribed medications, as well as with respect to refilling prescriptions therefor, performing various activities or keeping a doctor's appointment.

Moreover, at present health care providers such as physicians, pharmacists, and nurses do not have a suitable method of determining if patients are taking their medications as prescribed. This information is important for several reasons, including: (1) assisting a health care provider in assessing whether a lack of improvement in a patient's condition is due to noncompliance or to ineffectiveness of the medication or dosage, and (2) assisting with diagnosis and counseling based on the patient's pattern of compliance (e.g., is the patient forgetting or neglecting to take medications at night only; is the patient experiencing reduced cognition from the medication; etc.).

Indirect measures of compliance such as patient interviews and pill counts are only accurate approximately half the time. Direct measures such as blood tests (to determine medication levels) are costly, inconvenient for outpatients, and may be inaccurate due to varying metabolism and other factors.

There is thus a need in the prior art to provide compliance information to health care providers in order to develop the correct intervention for the patient's illness.

New burdens for the pharmacist have been legislated by the Omnibus Budget Reconciliation Act of 1990 ("OBRA '90"). Therein, all pharmacists are required to offer medication counseling to all Medicaid patients as of Jan. 1, 1993. Subsequent to the passage of this Act, at least 41 states have expanded the counseling requirement to all patients. In addition, various states are drafting standards that meet the Federal requirements, which require the following types of information to be provided for all prescription drugs: name and description of medicine, dosage form and dosage, how to administer, duration of drug therapy, how to handle missed doses, and prescription refill information.

Accordingly, there is a need for apparatus and methods for providing information which complies with the legislation and which helps the patient remember the information after leaving the pharmacy.

Moreover, it is difficult for the verbal counseling sessions to achieve their goals because patients often forget all or part of the message soon after the session is completed.

There is thus a need in the prior art for a device or method of repeating a counseling session for a patient, wherein the counseling information is repeated at the patient's convenience.

There is a more specific need to provide a "counseling message" that the user can access on the user device at any arbitrary time, as long as another message is not being played. A corollary need is for an ability to limit the number of times a counseling message can be repeated within a predetermined period of time in order to conserve power. A related need is to allow the counseling message to be programmed to play automatically at particular times and days.

The prior art discloses a number of devices that use electronic technology to remind users when to take their medication. These devices generally can be classified as:

(1) electronic timers/alarms, (2) medication dispensers combined with alarms, and (3) fixtures for holding medication containers which are combined with alarms.

As described in the following summary, most of the prior art requires the users to program the device themselves. A few references disclose methods that allow a pharmacist or another person to provide some level of programming. However, the prior art fails to provide devices meeting the above noted and long felt needs. The present invention thus provides new and improved features and methods which meet the above described needs, which overcome the deficiencies of the prior art, which can best monitor and improve health care compliance and which will provide increased acceptance of electronic reminder systems and dispensers by patients and health care providers.

Prior art in electronic timers and alarms for medication compliance, such as U.S. Pat. No. 5,200,891, typically require the user to program the device by using a variety of switches and buttons. The small buttons are difficult for elderly persons to operate, and it is both complex and intimidating for many patients, especially the elderly, to remember the sequence of operations and meaning of the buttons; even with the aid of text prompts on an LCD as provided in U.S. Pat. No. 4,558,303. Furthermore, it is left up to the patient to remember to reprogram the device every time the regimen changes and to do so accurately. U.S. Pat. No. 5,088,056 requires the user to operate a multiple mode switch depending on whether the medication is being taken as scheduled, ahead of schedule, or as needed. The added functionality thus results in added complexity, and discouragement, for the user.

There is thus a need in the prior art for medication reminders which do not require patient operated reprogramming, and which permit regimen programming by a health care provider.

Furthermore, total reliance on text messages, as described in U.S. Pat. Nos. 4,725,997, and 5,157,640, causes problems for the elderly, for users with low literacy skills, and for persons who are visually impaired. Such problems may arise because of glare from the LCD used therein or from the relatively small type size required for such "portable" devices. If the display size is increased to improve readability, then the reminder device becomes larger and less portable. In any case, the amount and type of information that can be communicated in text format at one time in a practical device is limited.

Medication reminder messages that are generated by speech synthesizers rather than LCDs or printed text are suggested in U.S. Pat. Nos. 5,088,056, 4,768,176, and 5,200,891. However, speech synthesis produces a "robotic" sounding voice that frequently is difficult for people to understand, particularly for the elderly, and which may discourage continued use of the device. Such difficulty in understanding is especially likely when complex words such as medication names are spoken. Presbycusis (i.e., age related hearing degradation) makes the task of distinguishing medication names even more difficult, especially when necessary to distinguish among names that sound alike or names that have higher frequency components. Research indicates that presbycusis is a widespread condition among the elderly population.

There is thus a need in the prior art for medication reminders which generate clear and natural sounding voice messages which are more easily communicated, more easily perceived, more flexibly changed, and more easily remembered than messages communicated through visual displays and alarms.

Research has shown that patients are not interested in a device that could potentially generate an audible tone or voice message in a public place or at a social gathering, because of a consideration that such medication information is private and confidential, and because of embarrassment upon public disclosure of the same. U.S. Pat. No. 5,200,891 addresses this issue by providing a "no-bell" button that suspends the audible tone for a predetermined period of time. The addition of another button on the surface of the device to perform this function further complicates its operation, however, and allows time to pass without informing the user that a medication needs to be taken.

There is thus a need in the prior art for medication reminder devices which have a capability for alerting the user at all scheduled times, such as by generating an audible or visual alert, which produce the voice messages only on demand by the user, and which produce the voice messages and any audible alert at a volume level selectable by the user.

Because of differences in age, state of health, weight, other medications being taken, and other factors, the instructions for two patients taking the same medication may vary considerably. Therefore, a system that relies only on fixed voice messages that are stored in a ROM (e.g., U.S. Pat. No. 5,088,056) may be very limited in applicability to the general population. Moreover, while some prior art devices are alleged to be portable, as more features are added to a reminder device, the power consumption, weight and size of the device increases. For example, a device disclosed in U.S. Pat. No. 5,088,056 must be plugged into an electrical outlet.

There is thus a need in the prior art for a device capable of generating a variety of customized reminder messages for any user for any medication, and for a device of sufficiently small size and weight as to be truly portable, having minimized power consumption.

In the prior art, medication reminders produce a fixed means of communicating with users. However, research has shown that different users have different cognitive abilities, and thus require different methods of communication. For example, some people prefer fast and concise voice messages to avoid loss of interest in and attention to the message content. Others require slower messages, with more words and pauses needed to comprehend the details. Cognitive skills and needs change over time and, in some elderly users, in response to use of certain medications that affect cognition. Such differences in cognitive ability and needs are not recognized by the prior art.

Thus, there is a need in the prior art for medication reminder devices which provide reminder messages tailored to the individual user, and which provide adaptive messages corresponding to particular situations, such as playing out but failing to confirm a particular reminder message, skipping of too many doses, or repeating of messages an excessive number of times. There is yet another need in the art to permit a health care provider to develop different message constructions to accommodate users with different cognitive skills, users whose cognitive skills decline, and users who become more proficient as they gain experience with the device.

There is still a further need in the prior art to provide a medication reminder device including logic for switching between one type of message construction and another, either adaptively or based on a predetermined schedule. Similarly, there is a need in the prior art for providing an adaptive volume control which increases the volume of a prompt and the generated message each time a user does not respond to a prompt or a message.

In the prior art, such as U.S. Pat. No. 4,258,354, audible and visual prompts are provided to remind the user about a medication to be taken. However, the art fails to recognize a large number of ways in which users may be interrupted in performing their tasks, such as by a telephone ring, a doorbell, another person talking, etc. These common interruptions are likely to arise occasionally at the time an audible prompt or a voice message is being played. The prior art fails to provide either a method or an apparatus to assist people who, for whatever reason, do not hear an audible prompt or miss some or all of a reminder message.

Thus, there is a need in the prior art for a medication reminder capable of repeating each segment of a message on demand one or more times, so that the user is confident that the entire message is understood. Along with such a needed capability, there is a related need to permit the health care provider to place a limit on the number of repeats for each message segment, to reduce power consumption.

In the prior art, several approaches are taken when the user does not respond to the prompting means. In some instances, such as in U.S. Pat. No. 5,157,640, the audible prompts continue indefinitely until the user responds. Other descriptions recognize that a continuous alarm that is turned off only when the user responds may consume too much power. Therefore, some prior art patents give the user one opportunity to respond to the alarm and then discontinue the audible prompt, while others repeat the audible prompt periodically, such as every 5 minutes (U.S. Pat. No. 4,768, 177) or every 5 seconds (U.S. Pat. No. 5,157,640) for a certain period of time such as ten minutes. While these and other devices will leave an LCD message or LED indicator on to alert the user that a medication needs to be taken, more information is needed by the user. In particular, while a device as disclosed in U.S. Patent 4,558,303 discloses avoiding overdosing by instructing a user not to take a dose with too little time remaining to the next dose, a user should receive more detailed instructions upon belatedly remembering to take a medication dosage close to the time of the next scheduled dosage. In such a situation, it is possible that one or more medication messages may become "outdated" because it is too close to the next dosage to take the medication, or it is time for the next medication as the dosage has been missed. It is usually unclear to the user whether to (1) skip that dose and wait for the next scheduled dose, (2) take the dose and also take the next scheduled dose, or (3) skip the dose but take a double dose at the next scheduled time.

There is thus a need in the art for a medication reminder device which informs the user in detail on the course of action to be taken in connection with a dosage being taken at other than a prescribed time.

Further, in some circumstances a patient is prescribed different medications that are to be taken at the same time. U.S. Pat. No. 5,157,640 establishes a queue of prompts and "uncovers" the next message in the queue after the user acknowledges the preceding beep. As previously noted, a problem arises when the user does not take a medication at the prescribed time.

One approach to resolving this problem is to specify a time interval within which the patient is allowed to take a medication and have it be effective. U.S. Pat. No. 4,725,997 refers to a "deviation window" and proposes to adjust the time interval between doses, and/or adjust the size of the dose to maintain an acceptable drug level in the patient. Such an approach could be very confusing to the patient in view of changes in the regimen on one or several days.

There is thus a need in the prior art for a medication reminder device and method which simplifies compliance for a user, and which only prompts a user to take a medication during the pharmaceutically correct time interval. More particularly, there is a need for a device incorporating logic and information which only prompts a user to take a medication within a predetermined "maximum effective time" (MET), and then stops prompting the user until the next scheduled dosing time. Thus, there is a need for a device capable of removing a message from a message queue when the MET of the associated medication has expired. There is an associated need to provide a medication reminder device which is capable of modifying the next scheduled message, after a medication dosage was missed, as and when new instructions are needed (e.g., "take 2 pills this time").

Moreover, to attend to situations wherein a plurality of medications are prescribed for substantially the same time, there is a need in the prior art for a device having an ability to provide, in a sequential fashion, prompts and messages that are scheduled for the same time of day, with a prompt and message being issued only after the preceding message has been issued and acted upon by either the user or the device.

Further, there are instances when a medication reminder may be in one location but the user may be in another, such as in two separate rooms, or when the level of background noise, such as a television, is sufficiently high that the audible prompt is not heard. To enable the user to take the required medications as close as possible to the prescribed time, it would be useful to have a supplemental way of communicating with the user that enhances the value of the user device.

Thus, there is a need in the prior art for a small, lightweight "satellite" device, which can nearly always be on the user's person or in the user's vicinity and which provides a prompting signal to alert the user to access a complete voice message from the "base station" user device.

U.S. Pat. No. 5,200,891 discloses interfaces between a prompting medication dispensing device and a variety of health care devices, such as pulse monitors, thermometers, blood pressure monitors and the like. The data are printed out, displayed, and entered into a memory. However, the user is not instructed on when to take the readings or what to do with the results.

Accordingly, there is a need in the prior art for a device to generate voice messages to remind the user to monitor temperature, pulse, blood pressure, etc.

There is still a further need to generate messages for guiding a user on taking specific actions with data that is transferred from external monitoring devices to the user device, such as "take a second reading", "call Dr. Smith", etc.

DISCLOSURE OF INVENTION

It is accordingly an object of the present invention to provide improved methods and apparatus for assisting a patient's memory with respect to timing, dosage, and counseling information relating to the patient's medications, as well as with respect to refilling prescriptions therefor, performing various health care activities or keeping a doctor's appointment.

It is a particular object of the invention to provide a health care compliance assistance system which is simple to operate and has reduced likelihood of confusion in operation, by minimization of the number of buttons provided therein and by providing different physical structures thereto.

It is a specific object of the invention to provide a health care compliance assistance system which does not require patient operated reprogramming, and which permits regimen programming by a health care provider.

It is still another object of the invention to provide a device for generating, in a sequential fashion, prompts and messages that are scheduled for the same time of day, with a prompt and message being issued only after the preceding message has been issued and acted upon by either the user or the device, thus to attend to situations wherein a plurality of medications are prescribed for administration at substantially the same time.

It is a more particular object of the invention to provide a health care compliance assistance system, wherein a user device provides compliance information to health care providers in order to develop the correct intervention for the patient's illness.

It is still another object of the invention to provide apparatus and methods for conveying counseling information to a user, and more particularly to provide a device or method of repeating a counseling session for a user, wherein the counseling information is repeated at the user's convenience.

It is an additional object of the invention to provide a health care compliance assistance system structured to enable a user to access a counseling message at any arbitrary time, as long as another message is not being played.

Yet another object is to provide a health care compliance assistance system wherein the number of times a counseling message can be repeated within a predetermined period of time is limited in order to conserve power. Still another object is to allow the counseling message to be programmed to play automatically at particular times and days.

It is a further object of the invention to provide a health care compliance assistance system which generates clear and natural sounding voice messages by using high performance compressed digital speech generation.

It is yet another object of the invention to provide a health care compliance assistance system which has a capability for alerting the user at all scheduled times, such as by generating an audible or visual alert, which produces voice messages only on demand by the user, and which produces the voice messages and any audible alert at a volume level selectable by the user.

It is still an additional object of the invention to provide a health care compliance assistance system for generating a variety of customized reminder messages for any user for any medication, and having minimized power consumption.

It is yet a further object of the invention to provide a health care compliance assistance system which provides reminder messages tailored to the individual user, and which provides adaptive messages corresponding to particular situations, such as playing out but failing to confirm a particular reminder message, skipping too many doses, or repeating messages an excessive number of times.

It is another object of the invention to provide a health care compliance assistance system including logic for switching between one type of message construction and another, either adaptively or based on a predetermined schedule.

It is a further object of the invention to provide an adaptive volume control which increases the volume of a generated audible prompt or message each time a user does not respond to a prompt or a message.

It is still another object of the invention to provide a health care compliance assistance system capable of repeating each segment of a message on demand one or more times, so that the user is confident that the entire message is understood. Along with such a capability, it is an object of the invention to permit the health care provider to place a limit on the number of repeats for each message segment, thus to reduce power consumption.

It is still a further object of the invention to provide a health care compliance assistance system which informs the user in detail on the course of action to be taken in connection with a dosage being taken at other than a prescribed time.

It is an additional object of the invention to provide a health care compliance assistance system and method which simplifies compliance for a user, and which only prompts a user to take a medication during the pharmaceutically correct time interval. More particularly, it is an object of the invention to provide a device incorporating logic and information which only prompts a user to take a medication within a predetermined MET, and then stops prompting the user until the next scheduled dosing time.

Still another object of the invention is to provide a health care compliance assistance system capable of adding a message to a message queue when the scheduled time of the associated medication has arrived, and removing a message from a message queue when the MET of the associated medication has expired, and which is capable of modifying a next scheduled message, after a medication dosage was missed, as and when new instructions are needed.

It is still another object of the invention to provide a small, lightweight satellite device on the user's person or in the user's vicinity which provides a prompting signal to alert the user to access a complete voice message from the base station user device.

It is yet an additional object of the invention to provide a device to generate voice messages for reminding a user to monitor temperature, pulse, blood pressure, etc. and to generate messages for guiding the user on taking specific actions with data that are transferred from external monitoring devices to the user device.

In accordance with the invention, there is thus provided a health care compliance assistance system, which is sufficiently flexible to be responsive to user compliance and noncompliance, as well as to express and implied user needs, to provide counseling messages and to modify the initially programmed operational sequences. Rather than merely providing an inflexible audible reminder to take medication, the invention reminds the user about a message, awaits user request for the message and confirmation of compliance, records user activity and modifies output messages.

More specifically, in accordance with one aspect of the invention, there is provided a health care compliance assistance system, including a host system and a user device. The host system includes an input device for inputting speech message data, user data and medication regimen data; a host storage for storing the speech data, the user data and the medication regimen data; a programmed device responsive to the medication regimen data for generating a user file including speech data and scheduling times for generating a speech message corresponding to the medication regimen data; and a transfer device. The user device includes a user device storage for storing a user file transferred to the user device by the transfer device; a speech generator for generating a speech message corresponding to the speech data stored in the user storage; and a programmed controller for controlling the speech generator to generate speech messages interactively with and responsive to a user.

In accordance with one feature of the invention, the transfer device may include a cable connecting the host system to the user device.

The host system may include a speech compressor for compressing speech data inputted by the input device for storage in the host storage. The host storage may include a storage area for storing the speech data in compressed digital format. In such an embodiment, the transfer device transfers the compressed speech data to the user device, the user device storage stores the compressed speech data, and the speech generator includes a speech decompressor for decompressing compressed speech data retrieved from the user device storage.

In accordance with another aspect of the invention, the user device may include a clock for determining a present time, and the programmed controller includes a timer for detecting correspondence between a predetermined medication scheduling time in the user file and a present time, and for controlling the speech generator to generate a speech message corresponding to the predetermined scheduling time upon detection of the correspondence.

In such an embodiment, the programmed controller preferably includes a queue generator, for detecting the existence of a plurality of substantially identical scheduling times in the user file corresponding to a common time and for establishing a queue of messages having the substantially identical scheduling times.

The programmed controller may order the queue in accordance with increasing (or decreasing) maximum-effective-time (MET) data for medications associated with the messages having substantially identical scheduling times, and may control the speech generator to generate a speech message remaining in the queue and associated with a medication having a shortest (or longest) MET of speech messages remaining in the queue.

Moreover, in such an embodiment the programmed controller may be programmed to generate a user prompt indicative of a forthcoming speech message, to establish a predetermined first time interval, and to await an interactive user playback input within the first time interval prior to controlling the speech generator to generate the speech message.

The programmed controller is preferably programmed to re-establish the predetermined first time interval upon expiration thereof prior to expiration of a second predetermined time interval corresponding to the MET data associated with the speech message, and to await the playback input prior to controlling the speech generator to generate the speech message.

The host storage means may comprise storage for speech message data comprising message segment data including speech phrase data, the transfer means thus operating for transferring compressed speech message data to the user device. The user device storage operates for storing transferred speech message data in the user file. The user device may further include a playback input device for entering the user playback input, requesting playback of a scheduled speech message, and the programmed controller may be programmed for responding to reception within the first time interval of an input signal from the playback input device by retrieving from the user file first message segment data and controlling the speech generator to generate a first segment of a speech message.

Still further, the user device may comprise a confirm input device for entering a user input for confirming receipt of a speech message, and the programmed controller may be programmed for establishing a third predetermined time interval after controlling the speech generator to generate the first segment of the speech message and for responding to reception within the third time interval of an input signal from the confirm input device by retrieving from the user file subsequent message segment data based on information in the user file.

In order to conserve memory in the user device, the programmed device of the host system is programmed for conservation of memory in said user device by further including in the user file: segment structure data describing a sequence of message segments ordered in accordance with the medication regimen data, and phrase identifier data identifying speech phrases included in each message segment of the sequence of message segments; and the user device further includes a speech accessor for accessing a speech message corresponding to the medication regimen data by accessing speech phrase data corresponding to phrase identifier data included in message segments in the user file transferred from the host system and stored in the user device storage. In such an arrangement, the speech generating means operates for generating a speech message provided by the speech accessor.

Moreover, the programmed controller may be programmed to establish a third predetermined time interval after controlling the speech generator to generate the segment of the speech message, and to await an interactive user confirmation input within the third time interval prior to controlling the speech generator to generate a next segment of the speech message.

In accordance with another aspect of the invention, the user device further includes at least three interactive user inputs, including a first user input requesting playback of a timed speech message, a second user input for confirming receipt of a speech message, and a third user input requesting playback of an untimed counseling message. A prompting device is provided for generating a prompt to inform the user of a requirement for inputting a predetermined one of the first and second user inputs. In such a configuration, the programmed controller is programmed: to control the prompting device to provide a first prompt for a user to input the first user input during a predetermined first time interval and to control the speech generator to generate a speech message segment upon detection of input of the first user input during the first time interval; to control the prompting device to provide a second prompt for a user to input the second user input during a predetermined third time interval and to control the speech generator to generate a speech message segment upon detection of input of the second user input during the third time interval, and to control the speech generator to generate a counseling speech message upon detection of the third user input.

The prompting device may be arranged for generating a speech prompt message to prompt the user to input the predetermined one of the user inputs.

In this embodiment, the programmed controller is further programmed to repeat a speech message upon user repetition of the first user input, and to repeat a counseling message upon user repetition of the third user input. In order to conserve power dissipation, the programmed controller may be further programmed to limit a number of message repetitions within predetermined time intervals.

In accordance with one facet of the invention, a prompt is generated and a time count initiated, and the speech generator generates a speech message upon detection of a user response within a predetermined time interval.

In response to a number of user requested repetitions in excess of a predetermined threshold the programmed controller is further programmed to respond by controlling the speech generator to append, to a next message to be accessed thereby, a predetermined message indicative of excessive repetitions.

Further, the programmed controller may be programmed to maintain a database file identifying user compliance and non-compliance with a health care regimen. In maintaining the database file the programmed controller increments a count of missed opportunities to respond to the first prompt upon failure of a user to provide the first user input during the first time interval, and increments a count of missed opportunities to respond to the second prompt upon failure of a user to provide the second user input during the third time interval.

The programmed controller may also be programmed to maintain a database file identifying a need for refilling a prescription stored in the user file, by counting a number of times a user responds to the second prompt by providing the second confirm user input, by calculating a difference between a predetermined number of doses in the prescription and the number of second confirm user inputs provided in response to the second prompt, and by controlling the speech generator to generate a speech message directing the user to refill the prescription when the difference is less than a predetermined value.

In accordance with one feature of the invention, the user device may include a number of user inputs and a monitor connector for connection to a health monitoring device and for transmitting health monitor data to the programmed controller for storage in the user file. The programmed controller is programmed for responding to operation of a first of the user inputs by controlling the speech generator to generate a speech message directing the user to use the health monitoring device, and for responding to operation of a second of the user inputs by analyzing the health monitor data transmitted thereto and by controlling the speech generator to generate a speech message responsive to results of the analysis of the health monitor data.

In accordance with another aspect of the invention, there is provided a health care compliance assistance system, including: a host system having a host storage for storing compressed speech data and user file data; and a user device receiving user file data and compressed speech data from the host system for accessing compressed speech data corresponding to a speech message and for generating the speech message. The user device of this aspect of the invention includes a decompression device for decompressing the compressed speech data; a speech generator for generating a speech message corresponding to the decompressed speech data; a programmed controller programmed for executing a program for comparing a current time with a predetermined time preset in the user file data received from the host system and, upon detecting a match therebetween, for controlling the speech generator to generate a prompt, for initiating a time count and upon detection of a user response within a predetermined time interval, for controlling the speech generator to generate a speech message, thereby controlling the speech generator to generate speech messages interactively with and responsive to a user.

Upon detection of user failure to activate a confirm input means during a maximum-effective-time (MET) for a medication associated with the message segment, the programmed controller is further programmed to control the speech generator to modify playback of a subsequently scheduled message segment for the medication associated with the message segment.

A plurality of prompters may be provided, and the programmed controller may be programmed to control the speech generator to play out a message segment by providing an audible playback prompt to the user, awaiting user activation of a playback input request, controlling the speech generator to play out a message segment if the playback input request is activated during a first time interval, and controlling the speech generator to repeat the message segment upon detection of a repeated activation of the playback input request.

In such an embodiment, the user device may further include an adaptive volume control, which is responsive to absence of user request for playback after expiration of the first time interval following the playback prompt and before expiration of a second time interval for controlling a predetermined one of the plurality of user prompters to repeat the audible playback prompt at a higher volume level than the preceding audible playback prompt provided to the user.

In accordance with an advantage of the invention, the host system includes an input device for inputting user profile data, and a host storage for storing the user profile data. The user file transferred from the host system to the user device includes a prescribed medication regimen, and the programmed controller is programmed to control the speech generator to generate messages having medication dosage times established from the prescribed medication regimen in accordance with the user profile data.

Still another feature of the invention provides for the user device a remote satellite device and a transmitter for transmitting a signal from the user device to the remote satellite device. The remote satellite device includes a receiver for receiving the signal transmitted by the transmitter, and a prompting device controlled by the receiver for outputting at the remote satellite device a preliminary prompting reminder to the user in response to transmission of the signal by the transmitter of the user device.

These and other objects, features and advantages of the present invention will become readily apparent to those skilled in the art from the following description and drawings, wherein there is shown and described a preferred embodiment of the invention, simply by way of illustration and not of limitation of one of the best modes (and alternative embodiments) suited to carry out the invention. The invention itself is set forth in the claims appended hereto. As will be realized upon examination of the specification and drawings and from practice of the same, the present invention is capable of still other, different, embodiments and its several details are capable of modifications in various obvious aspects, all without departing from the scope of the invention as recited in the claims. Accordingly, the drawings and the descriptions provided herein are to be regarded as illustrative in nature and not as restrictive of the invention.

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings.

BEST MODE FOR CARRYING OUT THE INVENTION

Figure 1:
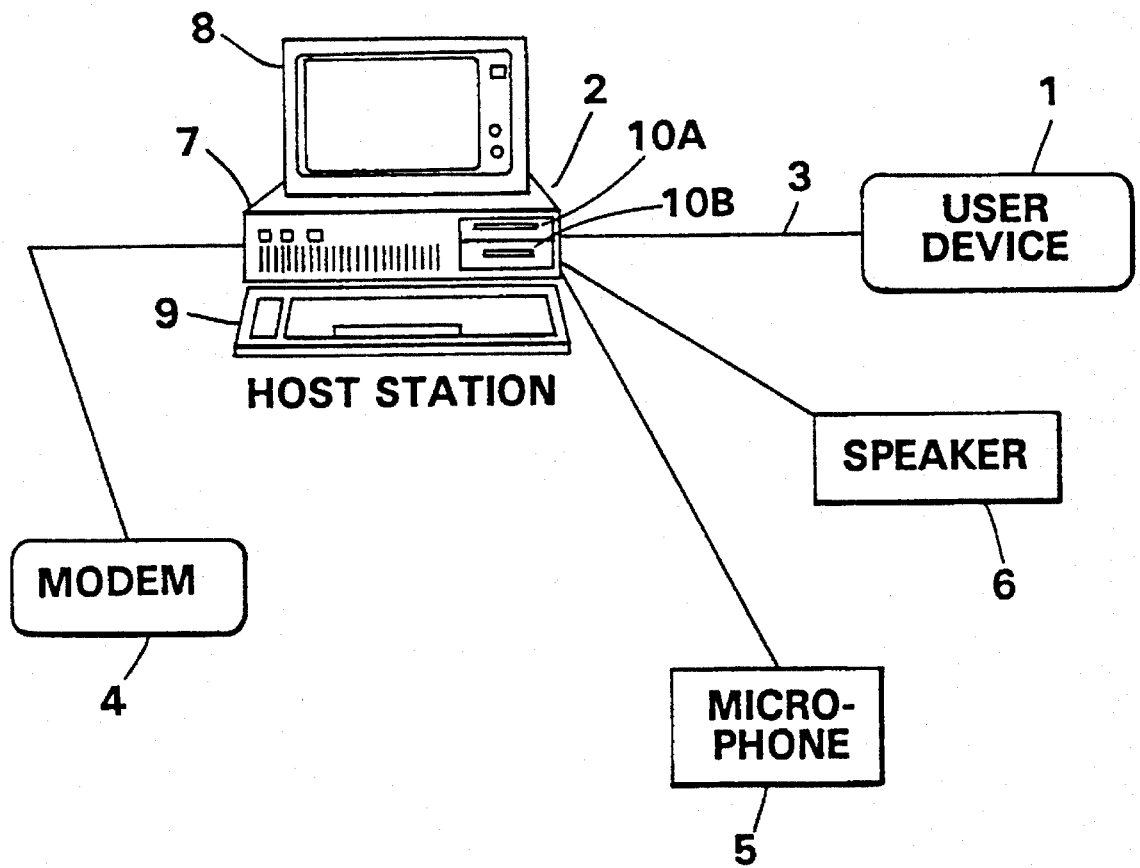
FIG. 1 is a sketch of a preferred embodiment of a system embodying the invention.

Referring now to the drawings, there is shown in FIG. 1 a sketch of a presently preferred embodiment of a health care compliance assistance system in accordance with the present invention. The system includes a user device 1, which is a portable or table top unit, that provides to a user medication reminders and other health care reminders, as well as counseling messages, in the form of voice messages and supplementary audible tone and visual prompting signals.

The voice, or speech, messages for non-medication health care reminders may be of the type "It is time to ride your exercise bike. After you ride your bike for 10 minutes, press the YES button." Upon user response by pressing the key identified in the message, the user device may generate a further segment of the speech message, such as "Thank you for riding your exercise bike."

A host station 2 of the inventive system may be a business or personal computer, such as is readily commercially available and generally identified as an IBM-compatible 386 or 486 system, including various input/output subsystems. A cable 3, typically several feet in length, connects the user device 1 to the host station 2, although other structures may be used to provide the connection.

In the presently preferred embodiment, a health-care provider for example, or another operator, may load data and software into the user device 1 by temporarily coupling the user device to the host station via the cable 3. Similarly, the user device may be connected to the host station by cable 3 in order to transfer data from the user device 1 to the host station 2. A modem 4 is used for connecting host station 2 to a network (not shown) of one or more related computers. A user device connected to the host station can thus be serviced by any computer or host station on the network.

The host station 2 is capable of performing the functions usually provided by medical prescription-filling computers. Software programs are commercially available for the host station to perform such functions, and are not part of the present invention. In accordance with the invention, however, the host station is also programmed to load data and software pertaining to voice reminders into a memory of user device 1, to extract and analyze data from user device 1, and to perform other functions in support of user device 1. As illustrated in FIG. 1, host station 2 includes a computer 7, a display such as a CRT monitor 8, although other display elements may be used, a keyboard 9, a hard (or fixed) disk drive 10A, a diskette (or floppy) drive 10B, and an optional CD-ROM drive for example. As is typical of commercially available computers, the computer, fixed and diskette drives may be enclosed in a common chassis, and the keyboard, display and other peripheral devices connected to the computer via various I/O (input-output) ports and connectors.

The host station 2 also contains an application program, a database and database software, which may be stored in a memory internal to the computer or may be externally stored (on the fixed disk or a diskette, or in a separate external storage device which may include magnetic tape). Host station 2 also includes a speech input/output circuit board, such as a circuit board commercially available from Texas Instruments under the designation TMS320C5x EVM illustrated in FIG. 3, and the modem 4. The speech input/output circuit board, schematically illustrated in the block diagram of FIG. 3, plugs into the main computer bus of host station 2. Cable 3 is coupled to the speech input/output circuit board, as is a microphone 5 and a loudspeaker 6.

The main components of the database contained in the host station 2 pertain to medication information, associated voice messages in a compressed digital format, information about each user, medication compliance information extracted from each user device, and a copy of the software and data needed for the operation of the user devices.

Compliance information is stored in the host station 2 as a record of the time and date of each key press on the user device by the user, and the time and date of each skipped dosage or skipped instruction.

The voice messages used in the present invention include one or more message segments. Typically two or three segments are used in a timed voice message. However, the number of segments is not restricted. A multiple-segment message can be used to particular advantage in several important ways. For example, the messages may be used to provide related operational instructions to the user, to provide information on medical appointments of the user, to provide medical counseling to the user, to confirm when the user has pressed the correct key, to add information needed for some users but not others, and to obtain user compliance data.

Figure 2A:
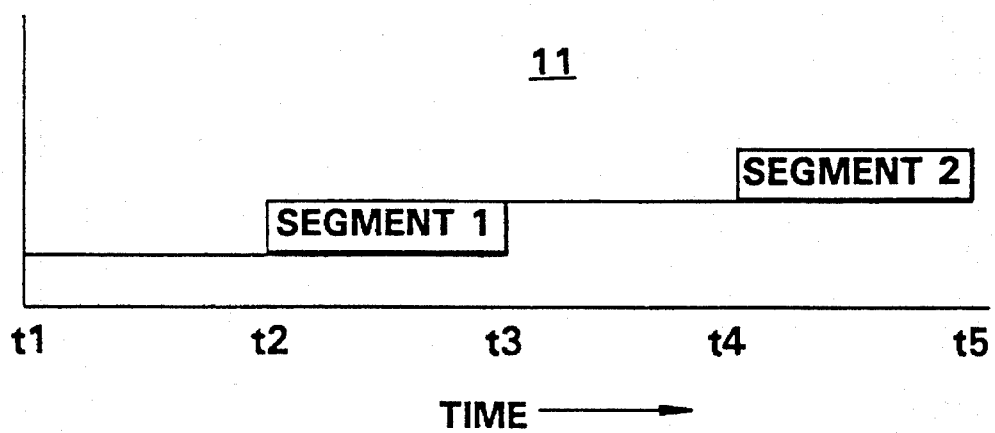
FIG. 2A illustrates the message and segment structure used in the invention.

FIG. 2A shows a simplified example of a 2-segment timed voice reminder message 11 as employed in the presently preferred embodiment. In FIG. 2A, the horizontal direction represents a time axis and the numerical designators t1, t2, t3, t4, and t5 indicate points in time. In the example, a first voice segment starts at time t2 and stops at time t3 (designated for brevity as time interval T23), while the second voice segment starts at time t4 and ends at time t5 (designated as time interval T45). In time interval T12, both audible prompts and first visual prompts are generated, or played out, and in time interval T34, second visual prompts are played out.

As will be understood from the subsequent description of the flow chart governing operation of the user device, at a starting time t1, timing circuits in the user device 1 detect that a time has arrived to play out one or more voice reminder messages. The user device 1 generates the audible tone prompt and first visual prompt at this time. At time t2, in response to the user pressing a specified user input control key on user device 1, the first segment of the first voice message is played. The user input indicates that the user is present and desires to hear the voice message. If the user is not present, or does not desire to hear the voice message at that time, the user can respond to a subsequent prompt. In the present example of a 2-segment voice message, the second visual prompt is turned on at a time t3 and stays on until time t4, when the user provides another input to user device 1. During time interval T45, user device 1 plays the second voice segment. Because this is a 2-segment message, no further actions are required on the part of the user.

Figure 2B:
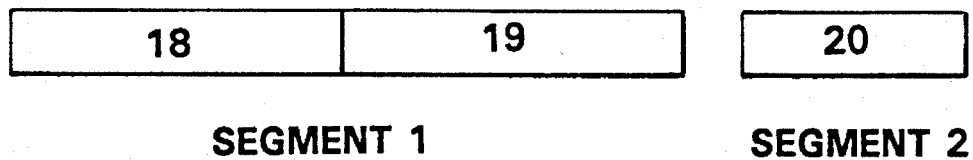
FIG. 2B depicts a segment to segment linkage structure for a message generated by the invention.

In order for the voice message to include more than lone segment, all the segments must be linked to each other. For example, in FIG. 2A, the first segment, in time interval T23, must provide a linkage to the second segment, in time interval T45. The linking technique is illustrated in FIG. 2B for this 2-segment message.

Figure 2C:
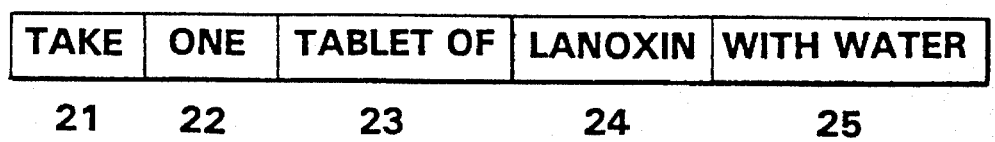
FIG. 2C illustrates the phrase structure for a segment used in the invention.

In this example, the first segment consists of two sentences 18 and 19. Sentence 18 may be a medical instruction such as "Take lone tablet of Lanoxin with water", formed of the phases 21–25 as shown in FIG. 2C. Sentence 19 is a special form which provides the desired linkage to the next segment in time sequence; it requests that the user respond, for example, by pressing a specified control key on user device 1.

Further, sentence 19 may be phrased to request that the user press the specified control key only if sentence 18 has been carried out. Such an approach permits logic in user device 1 to make an inference on user compliance with sentence 18 based on operation of the specified control key. For example, sentence 19 might be appended to the end of sentence 18 as follows: "Take one tablet of Lanoxin with water; after taking the Lanoxin tablet, press the YES key". Thus, upon detecting user activation of the YES key, compliance with sentence 18 may be inferred.

During interval T34 in FIG. 2A, the second visual prompt reminds the user to carry out both the instructions in sentences 18 and 19. In this manner, the second visual prompt and the specified control key supplement the linking technique. When, at time t4 in FIG. 2A, the user presses the specified control key to confirm that the instruction has been carried out, user device 1 generates the second and final voice segment (Sentence 20) during time interval T45. For example, the second segment may be "Thank you for taking a Lanoxin Tablet".

When a multiple-segment message is used and includes more than two segments, the interactive process hereinabove described is repeated until all remaining segments have been played. This enables the user and user device 1 to interact in a way that helps ensure that the instructions are carried out, further enabling user device 1 to make a compliance inference. The simplified description given here with reference to FIGS. 2A and 2B assumes the user responds to the prompts within predetermined time intervals. Additional details of operation of user device 1, and its detailed response to user controls relative to the predetermined time intervals, are described in connection with FIG. 6(A) to 6(F).

A sentence of a message segment is composed of one or more phrases and a phrase consists of one or more complete words. FIG. 2C illustrates the relationship between a sentence of a message segment 20 and the phrases of which it is composed. Due to the high degree of phrase repetition, decomposing instructions into phrases permits reduction of phrase redundancy and thus enables a much more efficient use of memory space in the user device 1. This is particularly important when storing a large number of messages in a single user device. Some of the phrases, such as the medication names (e.g., "Lanoxin") are specific to the medication and are denoted as "special phrases". The remaining phrases, such as "take" and "press the YES key" are used in nearly every medication message and are denoted as "common phrases".

In the present invention, voice phrases can be developed at a central location and transferred to host station 2 via diskette, CD, or telecommunications, for transfer to user device 1 as needed. It is feasible to store all common phrases in the memory of the user device 1, or in the memory of the host station 2, or both. It is also possible to store a large percentage of special voice phrases representing prescription medication names in the host station 2. From time to time, however, the digital voice form of a phrase such as a new medication name will not be present in the data base in host station 2. In this event, the health provider, or operator of the host station, can speak the phrase into microphone 5 as described in connection with the description of FIG. 3.

The memory of host station 2 contains a table of data representing each medication prescription. The data table contains all data pertinent to the prescription which will be transferred to user device 1, and includes the message segment structure, as well as identifiers of the voice phrases that comprise each segment, with the identifiers in time sequence corresponding to the order in which they are to appear when the message is played. Additionally, the data table contains all information on the times at which the message can be played. The data table also contains other parameters pertinent to the message, as defined in Table I, infra.

Each voice phrase identifier contains a code which indicates whether the actual voice phrase is located in user device 1, in host station 2, or neither. In the latter case, host station 2 prompts the operator, at the appropriate time, to record the missing voice phrase by means of microphone 5. Complete messages also can be stored in this manner, as further described in connection with FIG. 3.

When it is desired to specify a prescription for a user, a prescription code and all other data pertinent to the user, such as scheduled message times, are entered using the keyboard of host station 2. The default method for entering medication times is by entering the number of doses per day, coupled with program matching of the times to a prerecorded, customized, user profile. The program may adjust a message for a medication that has to be taken before or after a meal in accordance with the user's meal schedule. If other special restrictions or conditions are applicable, the specific times can be entered by the health care provider to overwrite the default values. This action generates the prompt which notifies the operator to record a medication name, for example, and then causes a file to be created in preparation for transfer to user device 1. The file thus includes the aforementioned table of data along with all voice phrases required to be transferred to user device 1.

The voice phrases included in the file transferred to the user device 1 are in compressed form, thus permitting faster transfers to user devices and requiring reduced memory capacity in the user devices. The quality of the decompressed analog speech output of user device 1 depends on the digital bit rate, or storage requirement, and on the nature of the compression/decompression algorithm used.

In 1993, the inventors hereof conducted speech-intelligibility experiments with senior citizens, in which complex medication names were played back using a high performance compression/decompression algorithm. The speech was compressed to 7200 bits per second and then restored. The high-quality voice output resulted in very good intelligibility. Subsequent tests of the same voice messages recorded at 4800 bits per second resulted in intelligibility that was not as good. These results illustrated the importance of high quality speech in a device of this type and provided a basis for preliminary estimates of the voice storage capacity required in user device 1. Other demonstrations by the inventors have shown that synthetic speech systems do not provide suitable intelligibility, especially when complex medication names are involved.

Figure 3:
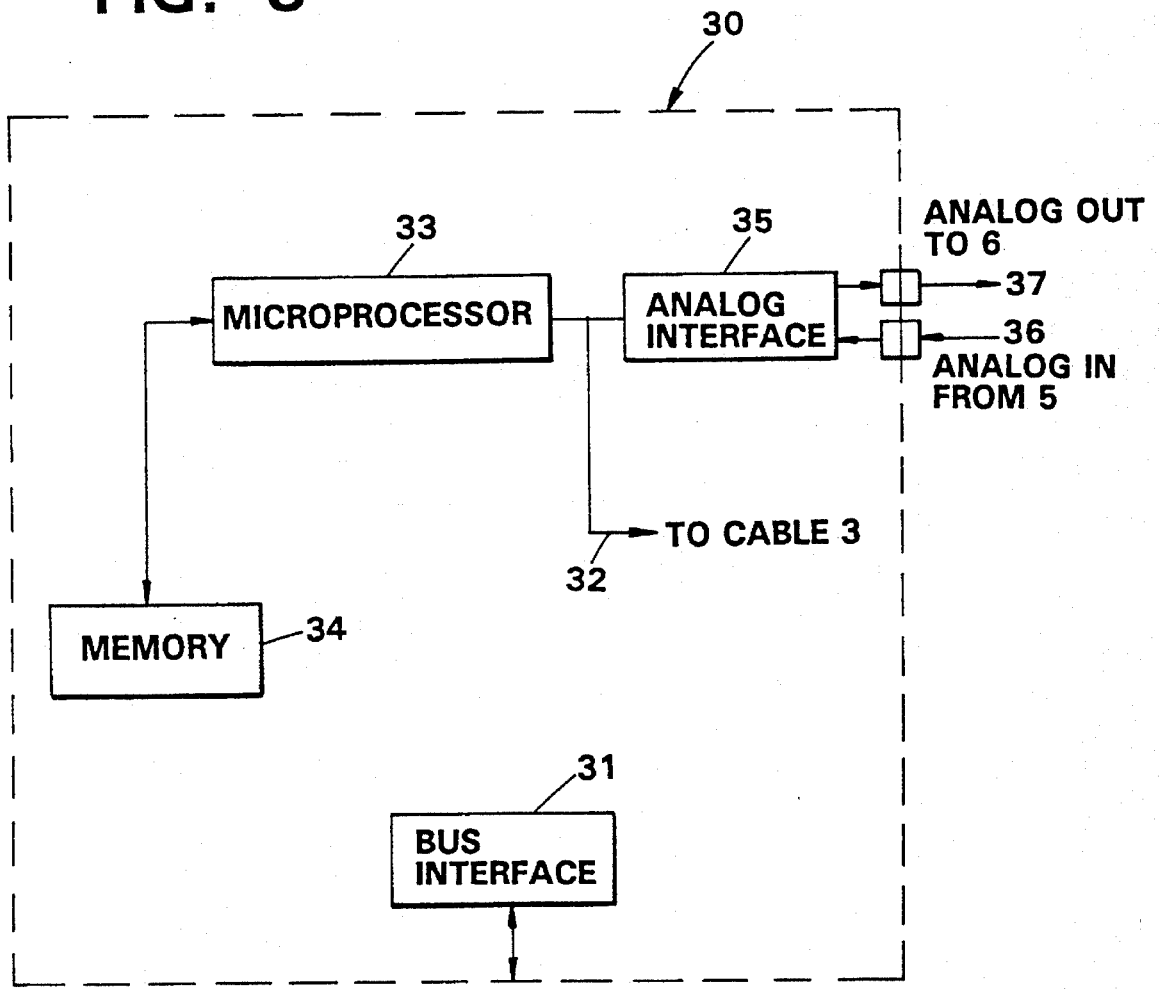
FIG. 3 is a block diagram of a speech I/O board circuit included in the host station of FIG. 1.

FIG. 3 is a block diagram showing the main circuit components of an illustrative speech input/output board 30 for host station 2. The requirements for board 30 can be met by a commercially available board typified by the TMS320C5x EVM from Texas Instruments. Included therein are circuits 31 for interfacing to the main computer bus, a path 32 which is coupled to cable 3, a microprocessor 33, a memory 34, an analog interface circuit 35, and connector jacks 36 and 37 for microphone 5 and loudspeaker 6, respectively. A compatible digital signal processor, such as the TMS320C5x, may also be used in user device 1.

The exemplary TMS320C5x EVM employs a Texas Instruments TMS320C50 digital signal processor for microprocessor 33. Thus, path 32 and the conductors of cable 3 would preferably carry the bi-directional serial port signals of the TMS320C50 digital signal processor.

As described above, the host station operator can enter a new message (including a counseling message), segment, or phrase via microphone 5. The resultant analog speech signal is converted to digital form in circuit 35, compressed, stored in memory 34 of the speech I/O board, and then transferred from the memory 34 through interface circuits 31 to the computer, whereupon the digital representation of the aforementioned message or name phrase is stored in the computer memory in a file associated with a particular medication prescription. If a counseling message is recorded, it is stored in a file associated with the user.

To preview the audio quality of a new segment, a display menu selection generated by the computer of the host station permits the operator to transfer the stored digital representation of the segment from the computer of host station 2 to memory 34 of the speech I/O board 30 for decompression and output to loudspeaker 6 via jack 37. When the operator is satisfied with the recorded segment, the operator can transfer the digital representation of the segment from host station 2 to user device 1 via microprocessor 33, path 32 and cable 3. The sound also can be previewed through a loudspeaker 60 in user device 1.

The compression-decompression function is performed by software residing in memory 34. A software algorithm which can provide the desired high quality output speech at loudspeaker 6 via jack 37, and most important, at a separate loudspeaker 60 in user device 1, is typified by a high quality CELP algorithm which is commercially available and licensed by several vendors. This type of software provides toll-quality speech at 8000 bits per second when the software runs on a TMS320C5x digital signal processor at 20 MIPS (million instructions per second). Approximately 10.3 million cycles are utilized each second when compressing, and 4.2 million cycles are utilized each second when decompressing.

Figure 4:
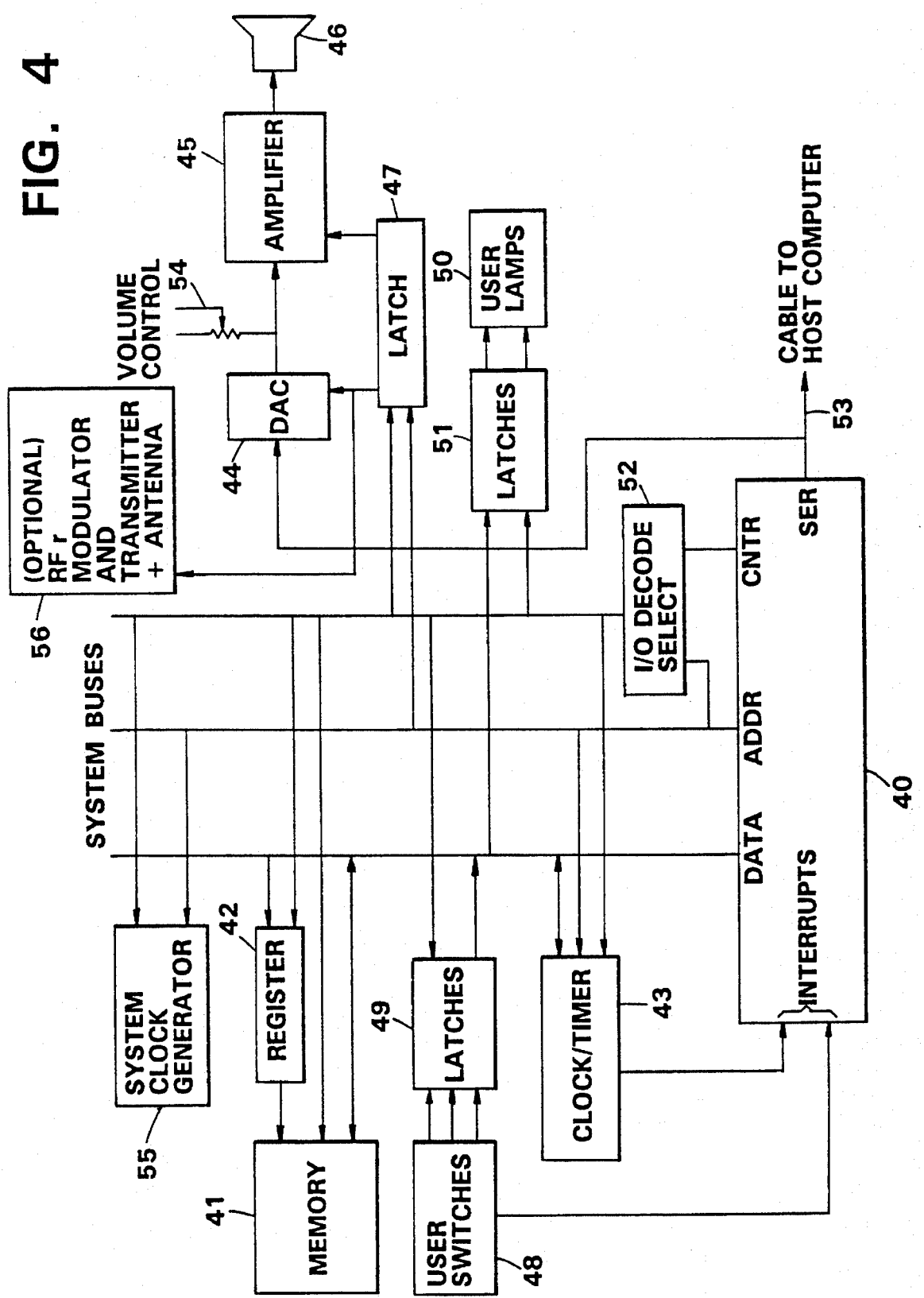
FIG. 4 is a block diagram of the user device of FIG. 1.

FIG. 4 is a presently preferred circuit diagram of user device 1, illustrating the main circuit components and their interconnections. An important criterion in the system design for the portable version of user device 1 is low power dissipation. A microprocessor 40 of the user device may be of the type available from Texas Instruments under the designation TMS320C52 digital signal processor chip. The TMS320C52 chip contains an internal 1k×16 bit high speed static RAM and a 4k×16 bit ROM. The internal RAM of the TMS320C52 is adequate for executing the high speed compression algorithm, and the ROM is adequate for keeping a copy of the compression algorithm, as well as other utility programs. An example of such utility programs includes a bootstrap program for downloading data to user device 1 from host station 2. As mentioned above, a high performance decompression algorithm is used.

Microprocessor 40 also executes the user device 1 application program which keeps time, issues reminders to the user, analyzes user inputs, and so on. An external memory 41, which is external to microprocessor 40 but is preferably internal to user device 1, preferably comprises a read-write memory section and, if needed, a static RAM section to supplement the aforementioned internal static RAM of microprocessor 40. The external read-write memory section included in memory 41 holds the user application program, the voice phrases, and various system parameters associated with operation of user device 1. A register 42 is provided therein to permit memory bank switching if the data memory required for voice messages is larger than the addressing space of microprocessor 40.

A nonvolatile read-write memory may be used as memory 41 in order to reduce power dissipation. Use of such a nonvolatile memory would enable common phrases to be permanently stored in user device 1, rather than being transferred when needed from host station 2. Such a nonvolatile memory chip which can provide the basis for the read-write memory section of memory 41 is typified by an Intel 28F008S flash memory chip.

A real time clock/timer 43 is included in the user device. Such a clock/timer is typified by a Dallas Semiconductor chip designated DS1605. This chip has a self-contained quartz crystal, as well as an internal lithium battery for maintaining time without external power. Microprocessor 40 can set an initial time and date in clock/timer 43, and can read the current time and date therefrom when needed. Microprocessor 40 also can set two alarm times in the clock/timer 43. When one of the set alarm times equals the actual time, real time clock/timer 43 issues an interrupt to the microprocessor 40.

A digital/analog converter 44, typified by a Texas Instruments TCM320A36 chip, is connected to receive digital output from microprocessor 40 via a serial port 53. The audio output generated by digital/analog converter 44 may be below the level needed to drive loudspeaker 60. Accordingly, an audio amplifier 45, typified by a Texas Instruments TLC2470 chip, is used to drive loudspeaker 60. Audio amplifier 45 additionally contains a volume control 54 at its input and provides filtering, which assists in smoothing any residual switching transients at the output of digital/analog converter 44. Digital/analog converter 44 can be powered down during standby periods by means of I/O addressing of a latch 47 by microprocessor 40 when neither voice messages nor audible tone prompting signals are being generated. When powered down, digital/analog converter 44 is effectively isolated from serial port 53. When a TLC2470 chip is used for audio amplifier 45, it is automatically powered down when its audio input signal is reduced to zero.

As people age, they are often affected by presbycusis, a condition characterized by reduced hearing acuity and difficulty in discerning hard consonants. This condition has been shown to increase the difficulty of distinguishing certain complex medication names by these persons. Therefore, user device 1 preferably includes an appropriate filter to increase the amplitude of the high frequency content components of the voice messages to produce increased clarity of speech. This filter may be designed as part of the audio amplifier 45, similarly to the above noted filter for switching transients. Similar technology is known to those skilled in the art and can be adapted for inclusion in the invention in conjunction with the design of the audio output components.

A Switching block 48 contains three user operated switches. An interrupt is generated, and a specific latch circuit 49 is set, when a given one of the switches in block 48 is closed. Lamps 50 are turned on and held on by a plurality of latches 51, which are selected by I/O addressing signals from microprocessor 40. Serial port 53 connects to the speech I/O board 30 in host station 2 via cable 3. A Circuit 52, typified by a Texas Instruments AS138 TTL decoder/demultiplexer, decodes address and control lines for the purpose of selecting the external peripheral chips in FIG. 4, as described. Microprocessor 40, if implemented with the chip TMS320C52, has 4 external interrupt pins. If an external interrupt comes into microprocessor 40, the interrupt may be taken, in which case microprocessor 40 will execute an interrupt service routine, or the interrupt can be tabled and handled by microprocessor 40 at a later time.

Microprocessor 40 is typically the largest source of power dissipation in user device 1. Power dissipation is proportional to the clock rate required by the microprocessor 40 to execute the real-time decompression algorithm program. The decompression algorithm is said to utilize only 4.2 million cycles each second when running at 20 MIPS. Accordingly, the clock can typically be set at approximately 4.2 megahertz, with the exact value determined by other clocking requirements, such as for serial port 53 and for digital/analog converter chip 44.

In the time intervals immediately before and after running the application program, the utilization of microprocessor 40 by the user application is extremely small in contrast to the approximate 5–10 second period typically required to decompress a voice segment. As a consequence, during these periods the user application program can be run at the same clock rate as the high speed decompression program without a significant power dissipation penalty. The TMS320C52 has a "sleep mode" in which the clock is effectively removed from the chip and all internal activity is halted. During the sleep mode, all internal contents are maintained and power dissipation is in the low microwatt range. The normal operating mode can be restored by means of an external interrupt.

Because the TMS320C52 chip is a fully static-type device, it can operate at a very low clock rate. The user application program can cause power dissipation to be decreased during standby periods by causing a system clock generator 55 to be switched to a low clock rate immediately before placing microprocessor 40 in the sleep mode. This strategy is important for those periods when voice messages are not required. When an external interrupt finally arrives, microprocessor 40, which had been in the sleep mode, is restored and initially operates at the low clock rate. While operating at the low clock rate, the application program can choose to maintain the low rate, or may switch to the high clock rate, for example, if it is necessary to run the decompression program. Since a clock generator circuit capable of functioning as described can be readily implemented by persons skilled in the art, the details of circuit 55 are not described.

The basic power management scheme for microprocessor 40 is as follows. When the generation of a voice message or an audible prompt is completed, the user application program assumes software control of user device 1. Then, as dictated by a combination of the program and the state of user device 1 for example, the program causes a lamp to be switched on, causes an appropriate alarm time to be set in real time clock/timer 43, and causes the clock generator to be set at the desired rate. Once these application tasks are completed, the program places microprocessor 40 in the low power "sleep" mode.

The low power mode is maintained until microprocessor 40 receives an interrupt from timer 43 or from the appropriate switch in block 48. After an interrupt occurs, microprocessor 40 returns to its normal operating mode at the previous clock rate. Once information is obtained on the nature of the interrupt, the user application program again takes over control of user device 1.

Figure 5:
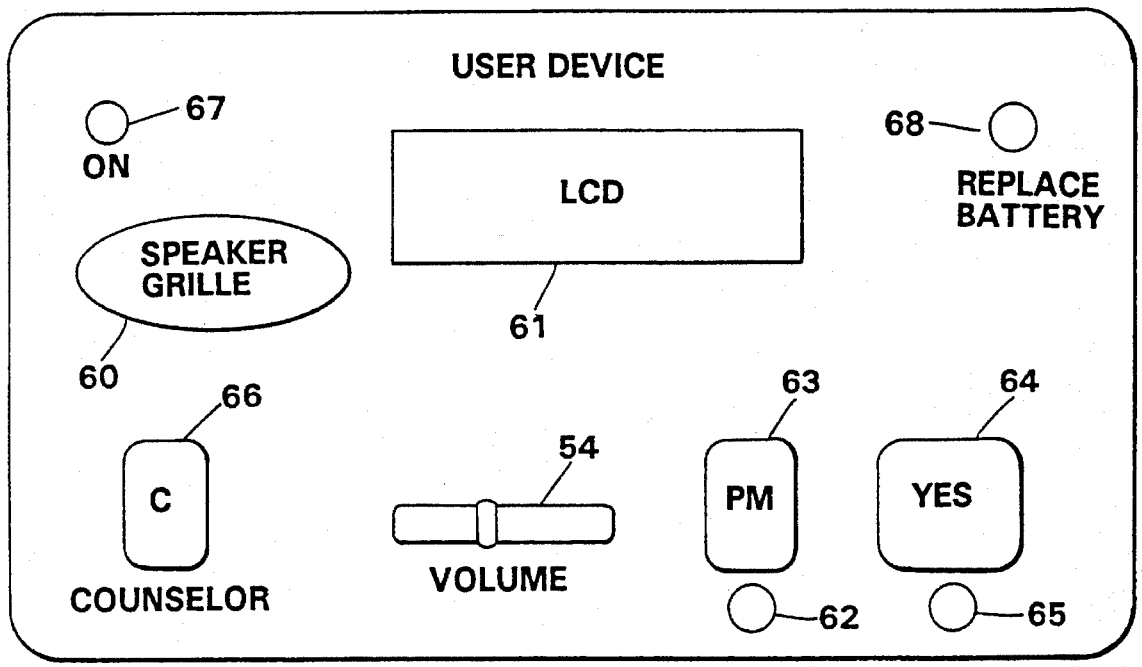
FIG. 5 is a plan view of the user device of FIG. 1.

FIG. 5 is a plan view of the portable version of the presently preferred user device 1 showing the main external user controls. The portable version of user device 1 operates by means of self-contained batteries. These batteries may be rechargeable by external recharging systems and/or by solar cells. In the user device 1, a loudspeaker 60 is used for converting voice messages and audible tone prompting signals to sound. Volume control 54 allows the user to adjust sound intensity of the voice messages and the audible prompts by changing the gain of the audio amplifier 45 contained within user device 1. The volume control in the preferred embodiment is designed for a minimal non-zero, audible, sound volume at its lowest setting, so the user cannot inadvertently turn off the volume entirely and miss an alert.

In order to assure that a user who is temporarily beyond the normal audible range of user device 1 can nonetheless be alerted that a time has come to hear a voice message, the invention may include a short-distance wireless communication link. In this optional configuration of the invention, an RF modulator and transmitter-antenna combination 56 would be installed in user device 1, as shown in FIG. 4. A receiver-antenna tuned to the transmitter frequency (not shown) may be provided, for example, in a wrist watch-like satellite device worn by the user. The wrist watch-like device contains an audio output channel consisting of an amplifier and a small loudspeaker capable of issuing an alert tone to the user whenever a transmitted signal is detected. The transmitter is turned on and off by means of select signals issued by microprocessor 40, in the manner depicted for other input/output devices in FIG. 4. The transmitter is selected, for example, at those times during interval T1 when user device 1 generates its normal audible prompting signals. Alternative prompting methods that may be employed singly or in combination in the wrist-watch like device include a mild vibration, a simple voice message, and a text message on the device's LCD. Upon receiving this prompting signal, the user will go to user device 1 and press the PM key 63 to retrieve the message in the usual manner.

As shown in FIG. 5, a lamp 62 and the audible tone prompt both serve as first-stage reminders when one or more timed messages have to be played out. Preferably, lamp 62 is situated in close proximity to, or physically integral with, a key 63 to serve as a visual indicator to press the key. When lamp 62 is active during a specified first time interval, preferably microprocessor 40 controls the lamp to operate in a blinking mode, where the blink count equals the number of messages currently queued to be played back. Responsively to the user's pressing key 63 within the specified first time interval microprocessor 40 causes the first segment of the next voice message in sequence to be played out, and further causes the audible tone prompt, if still active, and lamp 62 to be switched off. Responsively to the user's pressing key 63 within a specified second time interval microprocessor 40 causes the last played segment to be repeated. To prevent excessive power dissipation, a software controlled limit on the number of repeated segments is provided. A lamp 65 is kept on by the microprocessor throughout a specified third time interval in a continuous or blinking mode, and is maintained on until key 64 is pressed or until the third time interval expires, whichever occurs first. Preferably, lamp 65 is located in close proximity to, or integral with key 64, to serve as a visual reminder to press the key. Pressing key 64 within a specified third time interval implies that the last instruction has been carried out and causes the next segment, if any, to be played.

Responsively to the user's pressing another key 66 microprocessor 40 causes a voice counseling message, of one or more segments, to be played out by the user device 1. In response to pressing key 66 again the microprocessor causes the counseling message to be replayed. The number of replays permitted within a predetermined time interval is controlled by a software limit. Lamp 67 is kept on, continuously or in a blinking mode, to indicate that user device 1 is operational. Lamp 68 is turned on and/or a voice message is played to indicate that the charge on the battery is getting low and that the battery should be recharged or replaced. The functions of lamp 67 and/or lamp 68 may be replaced by an LCD display 61 which also displays the time of day.

Definitions of parameters stored in operation of user device 1 are shown in Table I.

TABLE I

Default Patient Parameters

T1—Time to the next audible alert if the user does not respond to the previous alert
T3—Time for the user to respond with an input after a segment is played
T4—Time period established for limiting accesses of counseling message (untimed) that starts with user pressing "C" key.
NR—Limit on the number of repeats allowed for a segment
CNR—Number of repeats of counseling message allowed during time period T4.
NF—Number of doses prior to depletion of medication to start playing a refill reminder message.

Indices

J Index for segments in a message (i.e., J=1 for first segment)
J* Message segment appended to reminder segment when user plays message but forgets to confirm an action
R Counts number of repeats for a segment
D Index for number of doses a remaining in prescription Message Parameters ST Start time. The time that the first dosage should be taken
RT Reminder times for a typical day
SD Start Date. The date that the first dosage should be taken
RD Reminder dates if all days are not applicable
DI Date Intervals; e.g., if medication should be taken every other day, then DI=1
ND Number of doses provided to the patient
NJ Number of segments in a message (not including J*)
T2 Timing parameter equal to the maximum effective time, MET, of the medication For each segment: Assign the times and dates for "turning on" specific segments that are to be played only at specific times on specific dates The parameters of Table I are generally classified in five categories, including: Global parameters that are related to the operation of the user device 1; patient parameters that are set up as system defaults and which can be modified by the health care provider for each user; indices that are used to keep track of the number of repeats, doses, etc. in order to reduce power consumption and activate the adaptive logic at the correct times; segment parameters that control the activation or deactivation of each specific segment; and message parameters that are specific to each message stored in user device 1.

One of the most important parameters used in conjunction with the present invention is the period of time during which prompts are issued ("maximum effective time", or MET). The MET represents an interval during which the user may take the medication and maintain an acceptable level of medication in the blood without taking the dosage too close in time to the next dose. The MET is determined for each individual medication based on pharmacodynamic and pharmacokinetic principles. Data used to estimate the MET are found in references such as *Drug Facts and Comparisons* and *USPDI*. These average values are adjusted by the health care provider in accordance with the user's age, health status, and other factors. Thus, the MET represents a safe window of opportunity for a patient who has failed to take a medication at the prescribed time, within which the medication may still be taken. The duration of the MET window is determined by pharmacists based on the above principles and data. As hereinabove noted, OBRA '90 requires that pharmacists counsel patients including providing advice as to whether to take the missed dosage, skip the dosage, or double the next dose. The present invention provides such counseling to the user, as follows.

The MET is referred to as time interval T2 in the description of FIGS. 6A–6F. Once T2 expires, the user is no longer prompted by user device 1 to take the medication. The application of these parameters to the operation of the inventive system is described with reference to FIG. 6.

As previously noted, the inventive system maintains a database to keep track of user compliance with the various instructions. The data recorded in the database include the related message/segment, date and time for each key press, and all "med skip" and "yes skip" entries. These data are stored in user device 1, and are later transferred to host station 2. Control of user device 1 is described by the flow chart shown in FIGS. 6A–6F. As will be appreciated from the description thereof, and from the above discussion, the interactive and adaptive operation of the inventive system provides a significant improvement over the prior art. In accordance with the improvement, the operation of user device 1 proceeds as follows.

Figure 6A:
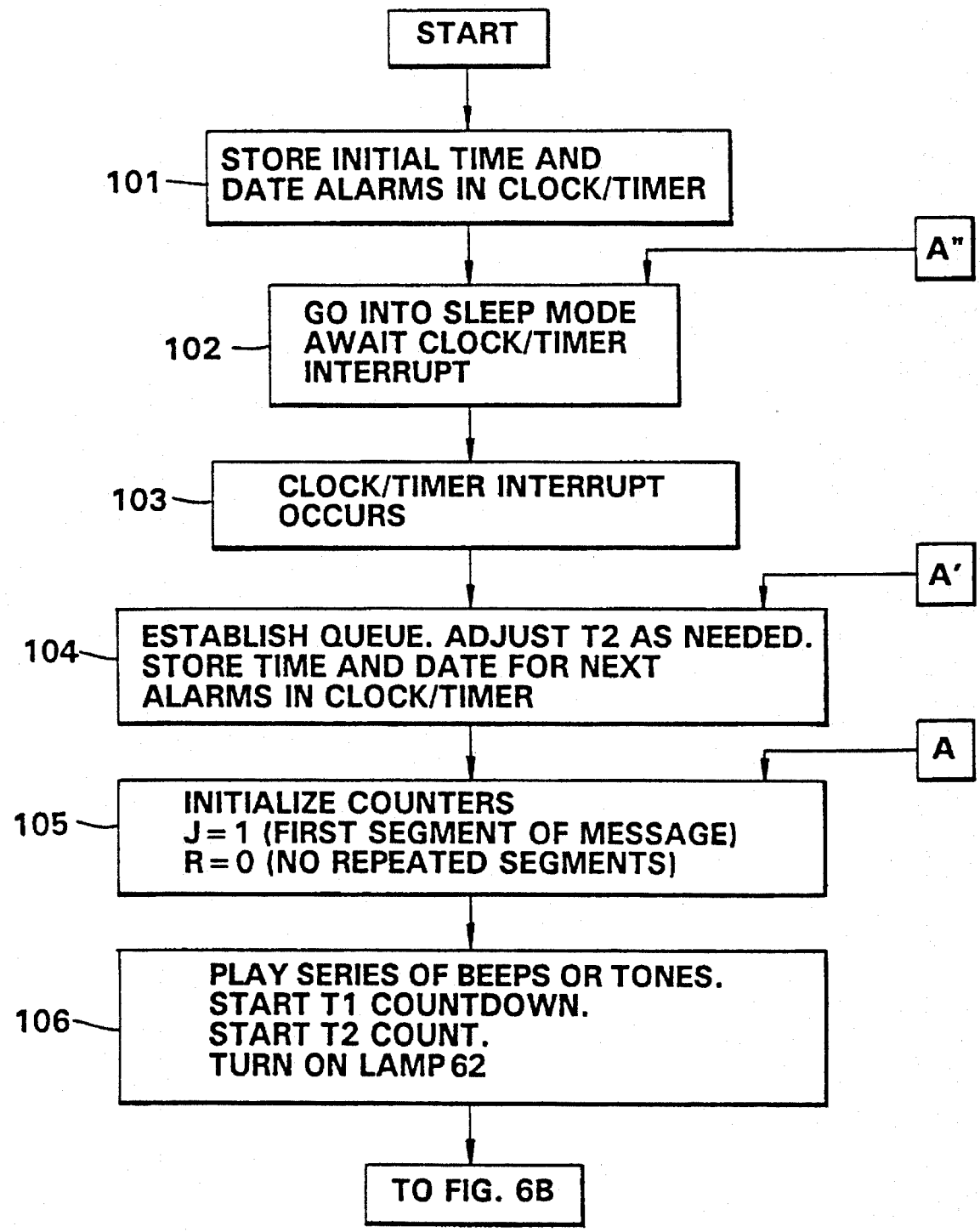
FIGS. 6A–6F are flow charts illustrating a main program controlling the processor of the user device of FIG. 3.

Preliminary to the operation sequence illustrated in FIG. 6A, microprocessor 40 is in a low power mode. In FIG. 6A, the activation date and time for a message (or queue of messages) is stored in the clock/timer chip in step 101. In this mode, microprocessor 40 waits for an interrupt from the clock/timer chip at step 102. When the current date and time equal the activation date and time, such as may have been transferred to the user device from the host station for the particular message being implemented, an interrupt from the clock/timer chip wakes up microprocessor 40 in step 103. All messages that match the date and time are then assigned to a queue and the date and time for the next alarm are stored in step 104. The messages in the queue are ordered according to the respective values of T2. The first message in the queue is the "active message". Ordering may be according to increasing or decreasing values of T2 associated therewith. A pair of counters J and R, which are useful in implementing the control sequence of FIGS. 6B–6F, are initialized in step 105.

At step 106, a series of audible prompting signals (e.g., a series of beeps or tones) and one or more visible prompting signals (e.g., blinking of lamp 62) are generated and countdowns start for the T1 and T2 parameters. Additional prompting signals that can be used in combination with the prompting signals include voiced speech prompts (e.g., "It's time for a message") and vibratory prompts. The audible and vibratory prompting signals indicate that at least one reminder message is to be played out, as do the visible and speech prompting signals which also indicate the number of messages in the queue and the identity of the key to press.

Figure 6B:
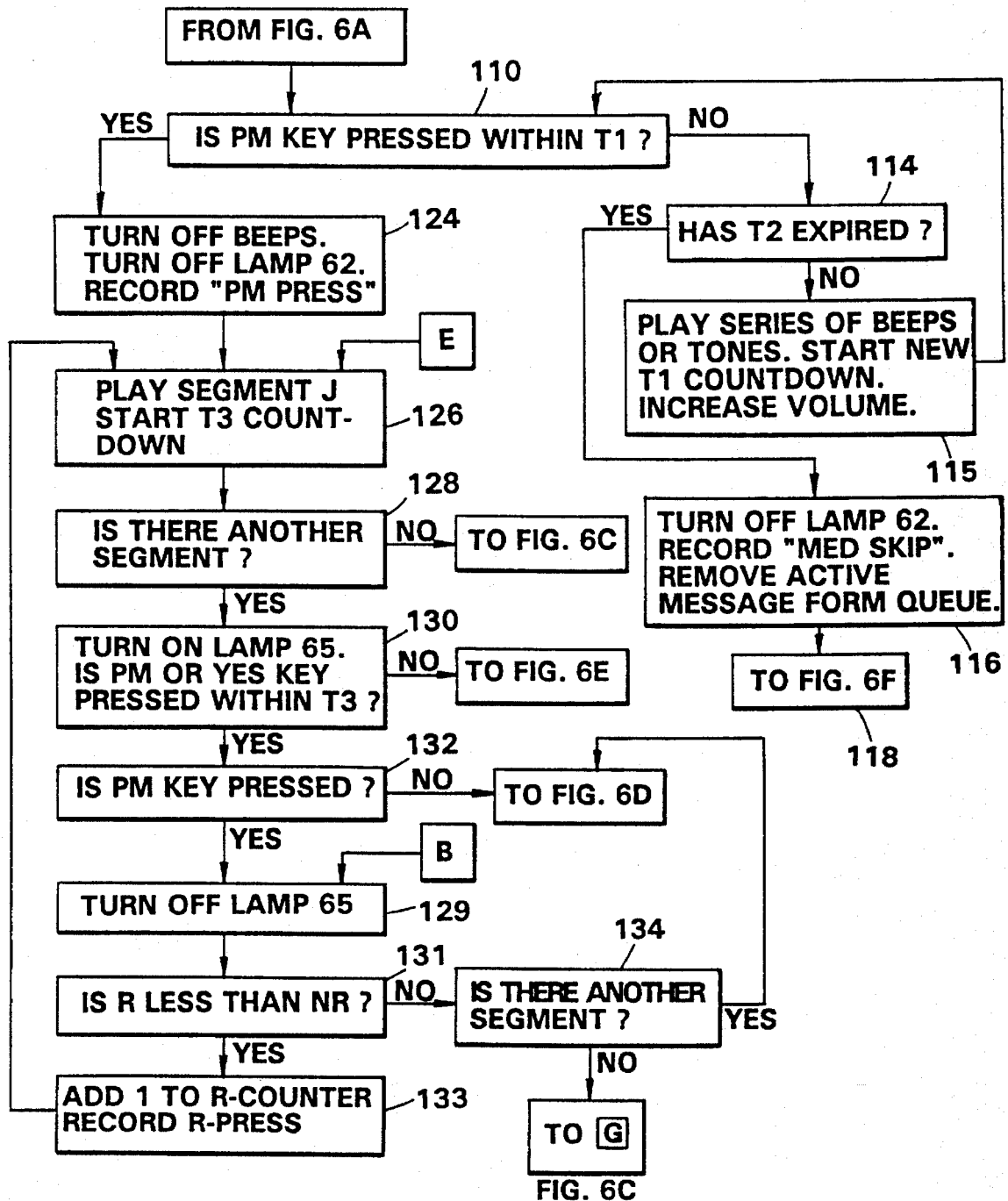

In FIG. 6B, at step 110, it is determined whether or not the PM key 63 is pressed (to play the active segment) during the first time interval T1 which, in practice, may be approximately 30 minutes. If the PM key 63 is not pressed prior to expiration of T1, the program executes the following sequence of steps. At step 114 it is determined if second time interval T2 has expired. If T1 has expired but T2 has not expired, then in step 115 the T1 count is restarted, another series of beeps is played, and the volume of the beeps is increased electronically by an amount determined by a volume parameter (which in practice may be 10 percent). Thus, the invention provides a prompt to the user, preferably an audible prompt (such as speech, tone, or the like), to indicate that a message awaits playback. Adaptively to failure of the user to respond by activating the PM key 63 within time T1, and as long as T2 has not yet expired, the user device repeats the audible prompt at an increased volume. Then, control branches back to step 110. Lamp 62 continues blinking throughout time interval T2 until the PM key 63 is pressed.

If T2 expires, lamp 62 is turned off, at step 116 a "med skip" datum is entered in the compliance database of user device 1, indicating that the user presumably did not take the medication, and the active message is removed from the queue. At this point, step 118 transfers control to the "queue check" procedure in FIG. 6F at step 163 where it is determined whether another message is in the queue. If there is another message in the queue, control branches back to step 105. If there are no other messages in the queue, the program checks for a timer interrupt in step 164, which indicates that the time for one or more new messages has arrived. If such an interrupt has occurred, control transfers to step 104 where a new queue is formed, as described above, and the T2 parameter for each message in the new queue is adjusted to account for all time since the originally scheduled message time. If no timer interrupts have been issued since the most recently active queue was established, control branches back to step 102 to await a timer interrupt.

An adaptive feature of the invention that arises after a "med skip" is recorded is the follow-up action. When the user responds to the next alert for the skipped medication, an additional phrase will be appended on to (or substituted for) the medication instruction phrase so the user is provided with an accurate course of action, or is requested to call a health care provider. For example, if a double dose is required after skipping a dose, the phrase, "Take 2 Lanoxin" may be substituted for the phrase "take 1 Lanoxin". The program continues to use the modified message construction until the user confirms that the medication is taken, and then the message construction reverts to the original version.

In a similar manner, an adaptive message is generated if the user skips too many medications. This message, which can be generated when the user next complies with a message, may say "Please see your pharmacist to discuss your medications today." These adaptive features are not shown in FIGS. 6(A)–6(F). However, a small modification to the flow chart in FIG. 6, which will be clear to those skilled in the programming art, will implement this aspect of the invention straightforwardly and without undue experimentation.

Next, if it is determined in step 110 that the PM key 63 is pressed before the expiration of T1, the sequence of beeps and the blinking light in lamp 62 are turned off in step 124. A "PM press" datum is entered into the database of user device 1 at step 124, thus noting user activation of the voice segment at that date and time. At step 126, user device 1 plays the Jth segment of the active message of the queue and begins the count for the third timing parameter, T3. In practice, T3 is typically set at approximately 5 minutes.

As long as there is at least one segment remaining, the sequence of steps following play out and confirmation of medication is 128, 130, 132, 160, 161, and 162 prior to returning to step 126. Thus, if another segment of the active message exists (step 128), lamp 65 is activated in step 130 to prompt the user to press the "YES" key 64, to confirm a response to the message. Also in step 130, it is determined whether either the PM key 63 or the YES key 64 is pressed within time interval T3.

If the YES key 64 is pressed during time interval T3 (FIG. 6D, step 160), lamp 65 is turned off and at step 161 a "YES press" is recorded in the database in user device 1. The "YES press" implies user compliance with the instruction in the segment. Step 162 increments the segment counter (J counter) to advance to the next (J+1st) segment of the message and resets the R counter to zero to reflect that the next segment has not been repeated. Control then returns to step 126 where the J+1st segment is played and the program continues until the last segment of the message is played.

If the PM key 63 is pressed (to repeat the segment) at steps 130/132, control proceeds to step 129 where lamp 65 is turned off and a "repeat loop" is initiated. The repeat loop limits the number of segment repetitions to conserve power. At step 131, it is determined if the limit on the number of permitted repetitions has been exceeded. If the repeat limit has not been exceeded, then the repeat loop continues, the R-counter is incremented by 1 and an "R-press" is added to the user device 1 database in step 133. Control then returns to step 126 where the segment is replayed. If the repeat limit has been exceeded, then additional repeats are not permitted and control branches to step 134. Then, because there remains another segment to be played, program control branches to FIG. 6D, step 160, where it is determined if the user presses the YES key 64 within time interval T3. This branch was earlier described herein.

Another adaptive feature of the system is the ability to provide voice messages if the user is having difficulty with user device 1, as evidenced by activation of the repeat function an excessive number of times. If the number of repeats in a day (or other predetermined time period) exceeds a preset threshold (such as 9 repeats in 3 days), the user device 1 may generate a voice message such as "Please call a health care provider to review the operation of your unit". It will be appreciated that other similar adaptive segments can be played within the scope of this invention, based on the user's response or lack of response to the alerts and messages.

Figure 6C:
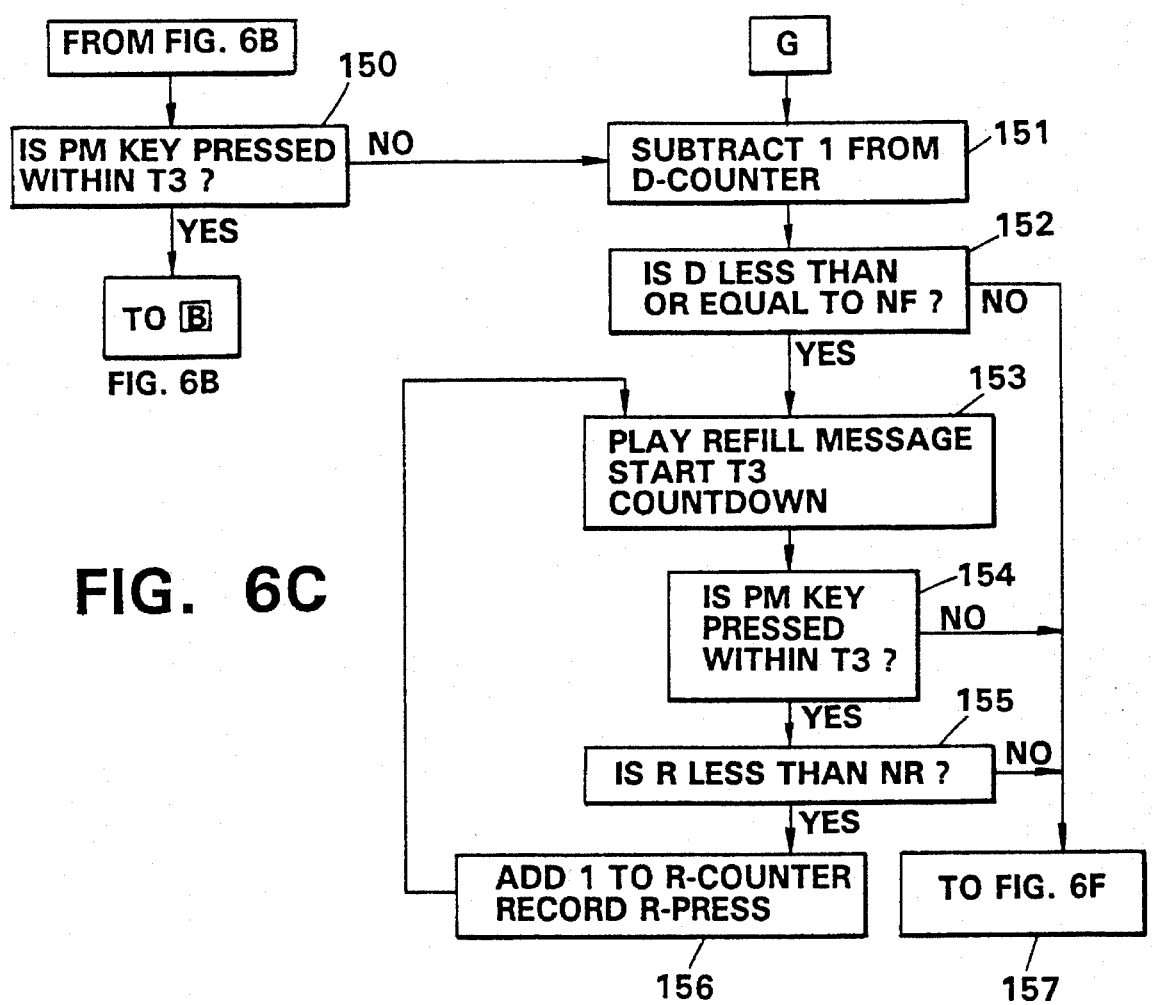
Figure 6D:
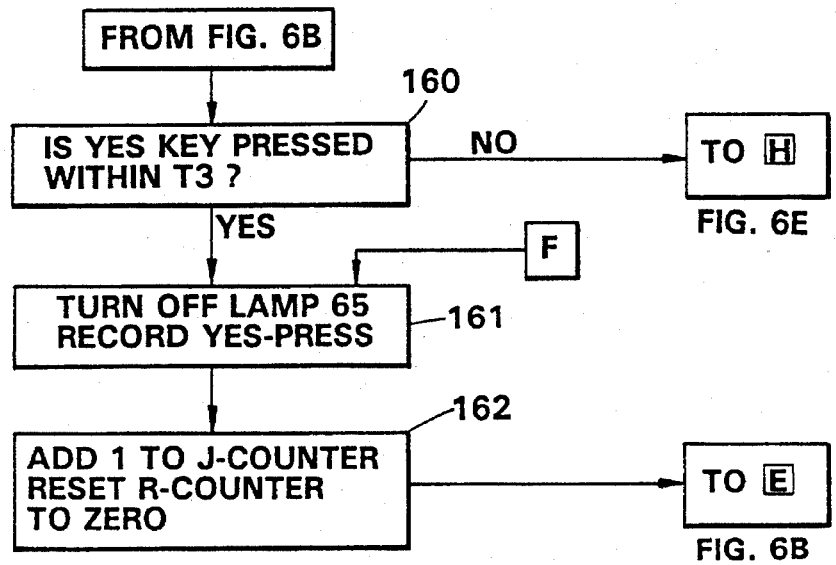

When the last segment of the message is active, control branches from step 128 of FIG. 6B to step 150 in FIG. 6C. By definition, a final segment of a message is one which does not require user feedback. Such final segments may include confirmations, such as "Thank you for taking a tablet", or warnings, such as "Do not drive your car for the next two hours". Thus, for a final segment of the message, no further activations of the YES key 64 are needed or monitored and a "YES skip" condition is not applicable. Therefore, in step 150, it is determined if the PM key 63 has been pressed within time interval T3 to repeat the final segment. If the PM key 63 is so pressed, control branches to the repeat loop starting with step 129 at FIG. 6B.

If the PM key 63 is not pressed at step 150, control branches to step 151 where the dosage counter is decremented by one. The dosage counter D is initially set to the number of doses included in a medication container dispensed to the user. Step 152 determines whether or not the remaining number of doses is below a predetermined threshold, NF, such as 4–10 remaining doses. If D is below the threshold, then a "refill" reminder message is generated at step 153, advising the user that a refill of the medication is needed, and a T3 count is started. An example of a refill reminder message is "It is time to refill your Lanoxin prescription. Please call your pharmacist at 555-1234 now, then press the YES button". This message will not be activated if the physician did not order a refill with the original prescription.

It is determined in step 154 if the user desires to repeat the refill message by pressing the PM key 63. If the PM key 63 is pressed within time T3, then a repeat loop is initiated at step 155, which tests if the predetermined limit of repeats, NR, has been exceeded, and at step 156, which increments the R counter by one and records an "R-press" in the database in user device 1. Control then returns to step 153 to replay the segment. If D is above the threshold limit in step 152, or the PM key 63 is not pressed within T3 in step 154, or the repeat limit has been exceeded in step 155, then at step 157 control branches to step 163 of FIG. 6F, which was described earlier.

Figure 6E:
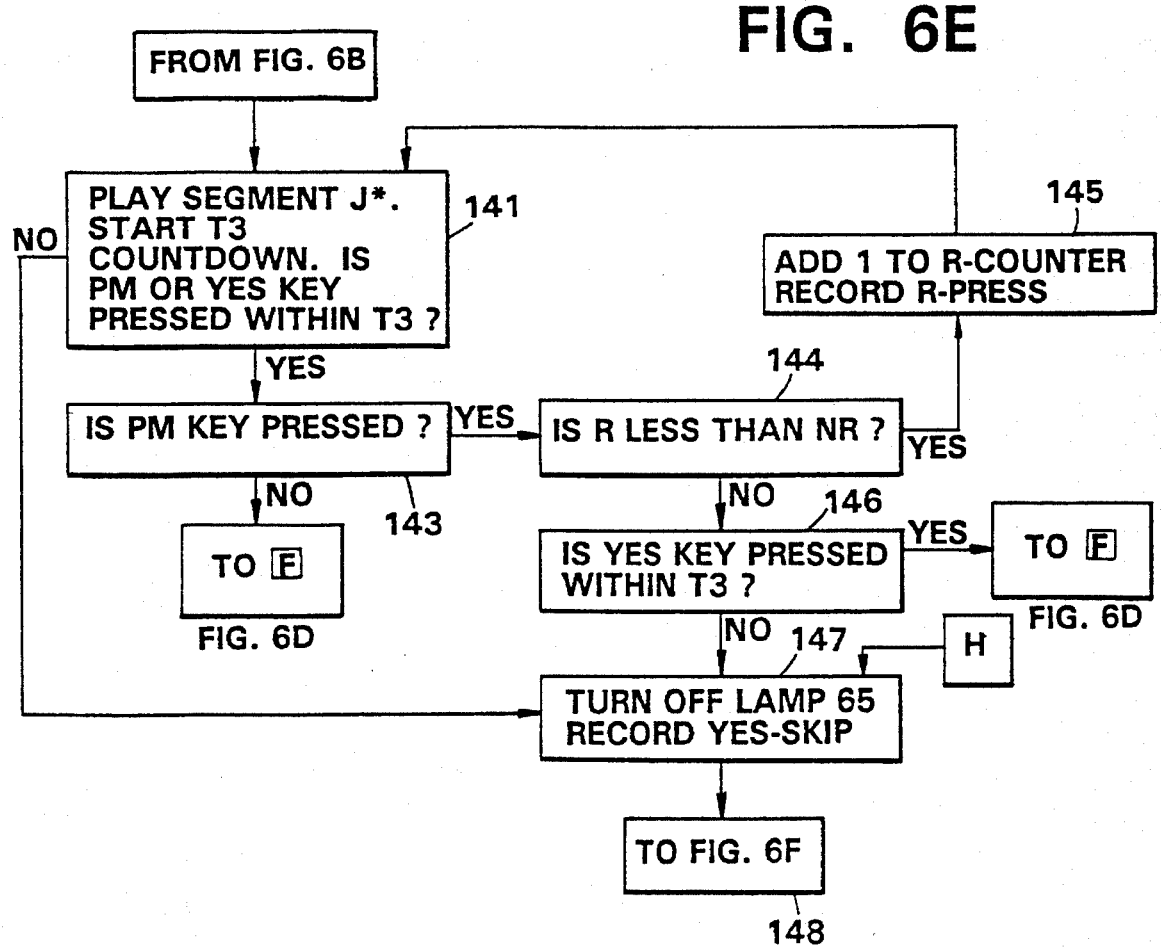

If the segment has been played, but the time T3 expires without either the PM key 63 or the YES key 64 being pressed, control branches from step 130 of FIG. 6B to the adaptive routine that starts in FIG. 6E, step 141. The user is provided a final opportunity to confirm compliance with the played out message segment. A modified segment is played out, including the segment that was not responded to within the time period T3, and an appended segment J*. For example, if the original message segment was "Take 2 Lanoxin tablets and press the YES button" then the modified segment may be "Please confirm the last reminder. Take 2 Lanoxin tablets and press the YES button".

Step 141 restarts the time period T3 to give the user an additional chance to activate either the YES key 64 or the PM key 63 before moving on to the next message. Thus, whichever key is activated first determines the control path to be followed. If the PM key 63 is pressed in step 143, and it is determined in step 144 that the repeat limit has not been exceeded, then the repeat loop is completed through step 145 (R is incremented by one and an "R-press" is recorded in the database in user device 1) and the return to step 141 where the segment is repeated. If the repeat limit has been exceeded, control branches to step 146. If it is determined in step 146 that the YES key 64 is pressed within time period T3, control branches to step 161 of FIG. 6D, where lamp 65 is turned off and a "YES press" is added to the database in user device 1. The segment counter J is incremented by one and the R counter is reset to zero at step 162, and then control returns to step 126 where the J+1st segment is played.

If it is determined at step 146 of FIG. 6E that the YES key 64 is not pressed within the new T3 time period, then at step 147 lamp 65 is turned off and a "YES skip" entry is added to the database in user device 1. At step 148, control then branches to FIG. 6F, step 163. This branch was earlier described.

Figure 6F:
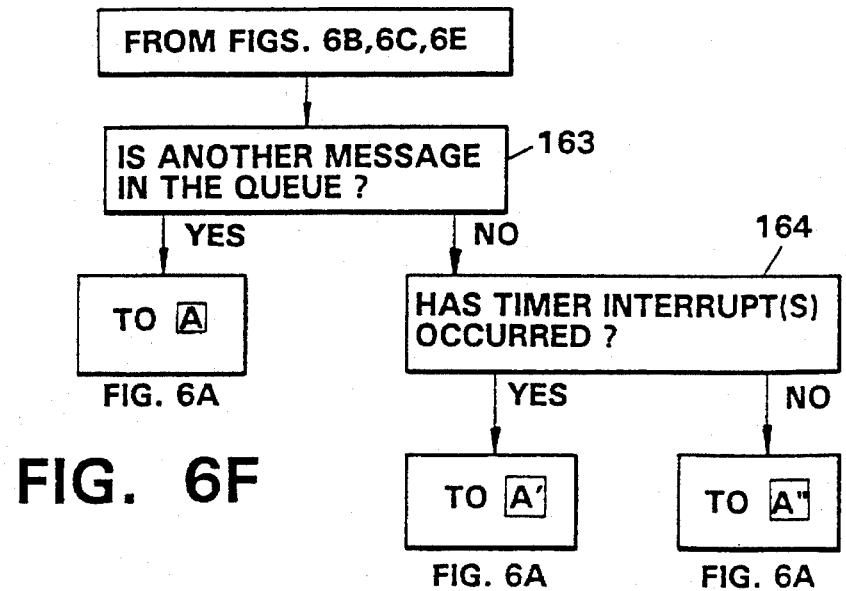

It will be appreciated that, at each of steps 118, 148 and 157, the inventive system branches to FIG. 6F, step 163, which implements a queue check, associated with an advantageous feature of the invention, which manages several messages that are scheduled for the same (or substantially the same) time.

In accordance with another aspect of the invention described above, user device 1 is programmed to provide counseling messages, which are typically generated when the user presses a third key 66, the "C" key. Thus, counseling messages such as "remember not to take aspirin without consulting with your doctor" may be provided, on an untimed basis, in response to a user request. The counseling messages may also be programmed for play out upon occurrence of a predetermined event, such as completion of the first dosage of the day, or for the first one or several days the user is on a new medication. Key 66 thus enables the user to access and repeat an untimed counseling message. The PM key 63 and YES key 64 are respectively used to play and repeat timed counseling messages in the same manner as other messages.

Figure 7:
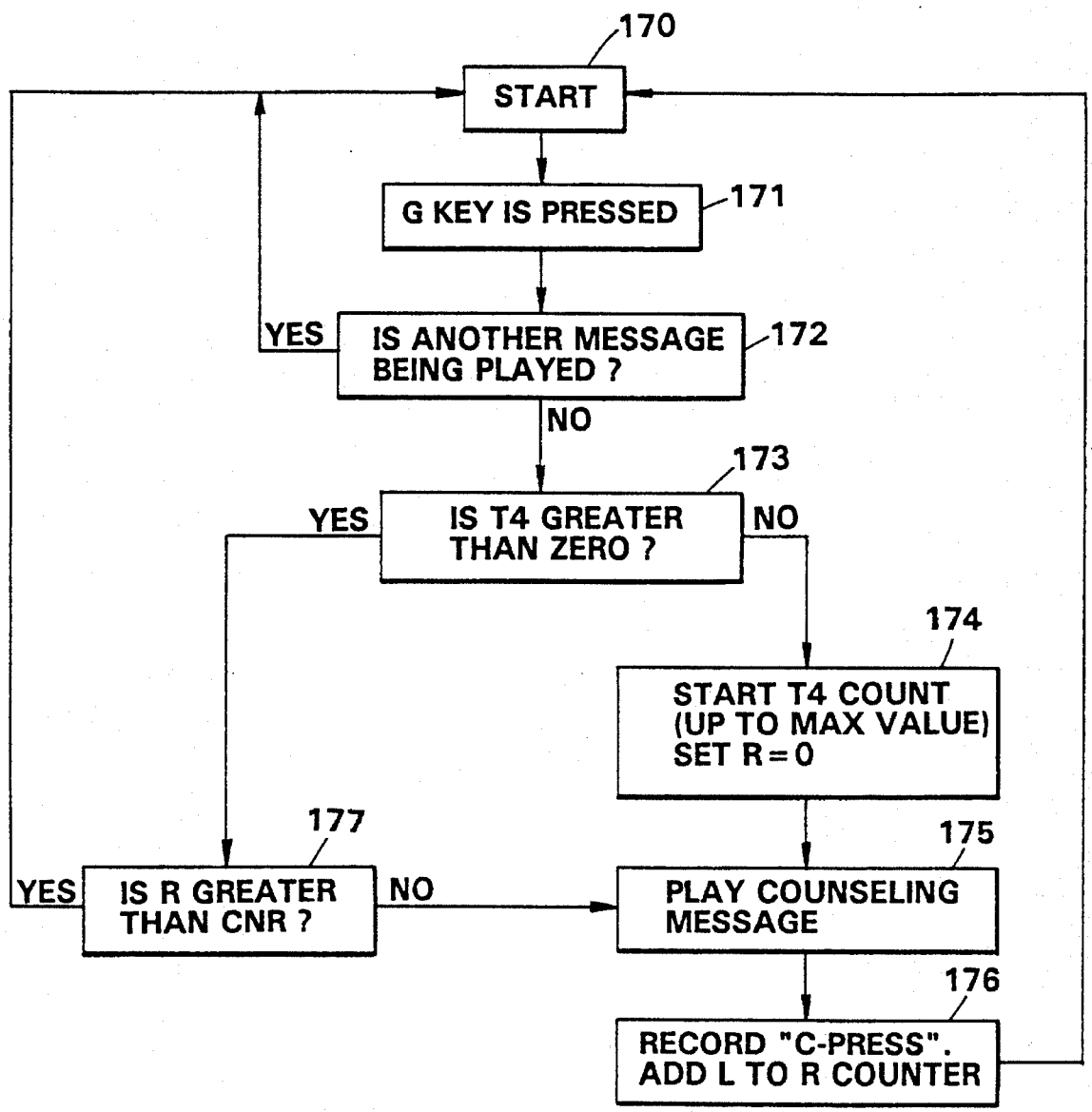
FIG. 7 is a flow chart of the program for the counseling messages.

The program governing the counseling message is shown in FIG. 7. The number of repeats of the counseling message is limited to a predetermined number each day (or other time period T4) to conserve power. The time interval T4 (typically 24 hours) and the repeat limit CNR (typically 3–5) are the controlling parameters.

Thus, at step 170 the system waits for activation of the C key. Upon determining at step 171 that the C key has been pressed, it is determined at step 172 whether another message is currently being played. If not, control proceeds to step 173 where it is determined whether a timer for time T4 has counted down to zero. If so, the timer is restarted at step 174 and the counseling message played at step 175. A "C-PRESS" datum is then recorded in the data base at step 176, the R counter is incremented by one, and the system returns to step 170 to await another operation of the C key. If at step 173 it is determined that the timer for T4 has a count greater than zero, i.e., that the period T4 has not expired from a previous activation of the C key, then step 177 is implemented to determine whether the C key has been operated more than the maximum limit (CNR) for the time period T4. If not, the message is played at step 175. If the limit has been exceeded, the system returns to step 170.

While details have been omitted relating to the manner in which file management, downloading, uploading and various other ministerial functions are carried out, such techniques are well known to those of ordinary skill in the art and do not, in and of themselves, form part of the present invention.

Although not illustrated in the drawings, an aspect of the present invention pertains to the use of the inventive system with one or more external health monitoring devices, such as a pulse- or blood pressure-reading device, a thermometer, or another data gathering device, to generate health care messages for the user. Various health care monitors are presently being marketed and are available to the user. Such monitors may contain a standard interface, such as an RS232 interface, which allows a hardware connection to other devices external thereto, along with internal software which allows these other devices to obtain a reading of a physical quantity when one is available. The monitoring device may thus be connected to the inventive user device 1 by means of an RS232 or a special customized interface. The monitoring device and user device 1 may operate in combination as follows.

The user may notify the user device 1 that a monitor is connected to the interface, by operating one or more of the control keys 63, 64 or 66, separately or in combination in a predetermined sequence or as a single operation. A separate monitor key may be provided. Alternatively, upon activation of a monitor connected to the interface, or upon connection of the health monitor to the interface, a predetermined interrupt may be provided, without requiring user operation, to inform microprocessor 40 of user device 1 that the specific health monitor is connected. Thereafter, by activating one or more of the input keys, such as the PM key 63, a speech message may be generated providing directions to use the monitor or instructions on how to use the specific health monitor.

The monitor then obtains a data reading of the particular parameter monitored thereby. Upon completion of the reading the monitor interrupts microprocessor 40 to store the data in memory 41. The user device application program then analyzes the data reading and, based on the results of the analysis, determines the follow-up action which, for example, might be generation of a speech message indicating the reading. Along with the reading message the user device may also provide an indication of a relation of the reading to a normal value for the user's characteristics. Depending on the magnitude and direction of a deviation between the data reading and the normal value, the user device may play out a further speech message directing the user to call a physician, to take a specified medication, or to take some specific course of action.

The foregoing description of the preferred embodiment of the invention has been presented for purposes of illustration and description. It is not intended to be exhaustive or to limit the invention to the precise forms disclosed, since many modifications or variations thereof are possible in light of the above teaching. For example, cable 3 could be replaced by various well-known communication techniques, including an existing telephone system or a wireless communication system using infra-red (IR) or RF communication. As another modification, various processing steps and programs for implementing the same have been disclosed as being implemented by the host 2 or by the user device 1. However, it is expected that the functions described as being performed by the host may be performed by programs in the user device, and that as size and cost of data processing equipment decreases and capability increases, the host system may become a portable device. Indeed, the system according to the invention may even combine the host system and the user device in a single portable structure so that all data is inputted to and processed by the single, portable, user device.

All such modifications and variations are within the scope of the invention. The embodiments described herein were chosen and described in order best to explain the principles of the invention and its practical application, thereby to enable others skilled in the art to utilize the invention in various embodiments and with various modifications as are suited to the particular use contemplated therefor. It is intended that the scope of the invention be defined by the claims appended hereto, when interpreted in accordance with the full breadth to which they are legally and equitably entitled.

What is claimed is:

1. A health care compliance assistance system, comprising:

a host system, including:
    input means for inputting speech data, user data and medication regimen data;
    host storage means for storing said speech data, said user data and said medication regimen data;
    programmed means responsive to said medication regimen data for generating a user file including said speech data and scheduling times for generating a speech message corresponding to said medication regimen data; and
    transfer means;

a user device including:
    user device storage means for storing said user file including speech data transferred to said user device by said transfer means;
    speech generating means for generating the speech message corresponding to the speech data stored in said user device storage means; and
    programmed control means for controlling said speech generating means to generate speech messages interactively with and responsive to a user, wherein said programmed means of said host system is programmed for reducing transmission and storage inefficiencies in said health care compliance assistance system by reducing transmission and storage of speech data for repeated portions of a specific speech message, and for causing said transfer means to transfer to said user device speech-portion identifiers instead of said speech data for said repeated portions.

2. A health care compliance assistance system according to claim 1, wherein said transfer means operates for transferring said user file including said user device speech-portion identifiers from said host system to said user device and further for transferring data within said user file, including user compliance data, from said user device to said host system.

3. A health care compliance assistance system according to claim 1, wherein said programmed means of said host system further comprises speech compression means for compressing speech data inputted by said input means for storage in said host storage means, said host storage means includes a storage area for storing said speech data in compressed digital format, said transfer means transfers said compressed speech data to said user device, said user device storage means stores said compressed speech data, and said speech generating means includes speech decompression means for decompressing compressed speech data retrieved from said user device storage means.

4. A health care compliance assistance system according to claim 1, wherein said user device comprises clock means for determining a present time, and said programmed control means comprises a comparison means for detecting correspondence between a predetermined speech message scheduling time in said user file and a present time, and for controlling said speech generating means to generate a speech message corresponding to said predetermined scheduling time upon detection of said correspondence.

5. A health care compliance assistance system according to claim 4, wherein said programmed control means comprises a comparison means for detecting existence of a plurality of substantially identical scheduling times in said user file corresponding to a common time and a queue means for establishing a queue of speech messages having said substantially identical scheduling times.

6. A health care compliance assistance system according to claim 5, further including means for assigning a respective predetermined time interval to each speech message representing a maximum-effective-time (MET) and for inhibiting generation of said each speech message by said speech generating means following expiration of said respective MET, until a next scheduled time for said respective speech message, and wherein said queue means is programmed for ordering speech messages having substantially identical scheduling times in said queue in accordance with increasing MET data, said programmed control means controlling said speech generating means to generate a speech message having a shortest MET of speech messages remaining in said queue.

7. A health care compliance assistance system according to claim 5, further including means for assigning a respective predetermined time interval to each speech message representing a maximum-effective-time (MET), and for inhibiting generation of said each speech message by said speech generating means following expiration of said respective MET, until a next scheduled time for said respective speech message, and wherein said queue means is programmed for ordering speech messages having substantially identical scheduling times in said queue in accordance with decreasing MET data, said programmed control means controlling said speech generating means to generate a speech message having a longest MET of speech messages remaining in said queue.

8. A health care compliance assistance system according to claim 5, further comprising means for assigning a respective predetermined time interval to each speech message representing a maximum-effective-time (MET) and for inhibiting generation of said each speech message by said speech generating means following expiration of said respective MET, until a next scheduled time for said respective speech message, and means for adding a specific speech message to said queue when the scheduling time of said specific speech message arrives, and for removing a speech message from said queue when a maximum-effective-time (MET) of said speech message expires or when the user responds to a generated speech message.

9. A health care compliance assistance system according to claim 5, wherein said programmed control means is programmed to generate a user prompt indicative of a forthcoming speech message, to establish a predetermined first time interval, and to await an interactive user playback input within said first time interval prior to controlling said speech generating means to generate said speech message.

10. A health care compliance assistance system according to claim 9, wherein said programmed control means is programmed to re-establish said predetermined first time interval upon expiration thereof prior to expiration of a second predetermined time interval corresponding to MET data associated with said speech message, and to await said user playback input prior to controlling said speech generating means to generate said speech message.

11. A health care compliance assistance system according to claim 9, wherein said host storage means comprises means for storing compressed speech data, said transfer means operating for transferring said compressed speech data to said user device, said user device storage means operating for storing transferred compressed speech data in said user file.

12. A health care compliance assistance system according to claim 11, wherein said user device further comprises:

playback input means for entering said user playback input requesting playback of a scheduled speech message, and said programmed control means being programmed for responding to reception within said first time interval of an input signal from said playback input means by retrieving from said user file first message segment data and controlling said speech generating means to generate a first segment of a speech message.

13. A health care compliance assistance system according to claim 12, wherein: said user device further comprises confirm input means for entering a user input for confirming receipt of a speech message;

said programmed control means is programmed for establishing a third predetermined time interval after controlling said speech generating means to generate said first segment of said speech message and for responding to reception within said third time interval of an input signal from said confirm input means by retrieving from said user file subsequent message segment data based on information in said user file.

14. A health care compliance assistance system according to claim 9, wherein said programmed control means is programmed to establish a third predetermined time interval after controlling said speech generating means to generate said segment of said speech message, and to await an interactive user confirmation input within said third time interval prior to controlling said speech generating means to generate a next segment of said speech message.

15. A health care compliance assistance system according to claim 1, wherein said programmed means of said host system is programmed for conservation of memory in said user device by further including in said user file: segment structure data describing a sequence of message segments ordered in accordance with said medication regimen data and phrase identifier data identifying speech phrases included in each message segment of said sequence of message segments; and said user device further comprising speech accessing means for accessing a speech message corresponding to said medication regimen data by accessing speech phrase data corresponding to phrase identifier data included in said message segments in said user file transferred from said host system and stored in said user device storage means;

wherein said speech generating means operates for generating a speech message provided by said speech accessing means. by limiting a number of repetitions of a counseling message within predetermined time intervals.

16. A health care compliance assistance system according to claim 1, wherein said user device comprises clock means for determining a present time, and said programmed control means comprises a comparison means for detecting correspondence between a predetermined speech message scheduling time in said user file and a present time, and for controlling a prompting means to generate a prompt for informing the user to provide a user playback input.

17. A health care compliance assistance system according to claim 16, wherein said programmed control means comprises a comparison means for detecting existence of a plurality of substantially identical scheduling times in said user file corresponding to a common time and a queue means for establishing a queue of speech messages having said substantially identical scheduling times, and a prompting means for generating said prompt for informing the user of a time to input said user playback input to generate the first of said speech messages in said queue.

18. A health care compliance assistance system according to claim 11, wherein said programmed control means of said user device is further programmed to generate speech messages from portions identified by said speech-portion identifiers by assembling said portions into speech segments and for assembling said speech segments into speech messages.

19. A health care compliance assistance system comprising:

a host system, including:

input means for inputting speech data, user data and medication regimen data;

host storage means for storing said speech data, said user data and said medication regimen data;

programmed means responsive to said medication regimen data for generating a user file including scheduling times for generating a speech message corresponding to said medication regimen data; and transfer means;

a user device including:
user device storage means for storing speech data and said user file transferred to said user device by said transfer means;
speech generating means for generating the speech message corresponding to the speech data stored in said user device storage means;
programmed control means for controlling said speech generating means to generate speech messages interactively with and responsive to a user;
means for entering at least three interactive user inputs, including a playback user input requesting playback of a scheduled speech message, a confirming user input for confirming receipt of the speech message, and a counseling user input requesting unscheduled playback of a counseling message; and
prompting means for generating a prompt to inform the user of a requirement for inputting a predetermined one of said playback and confirming user inputs;
wherein said programmed control means is programmed to control said prompting means to provide a first prompt for a user to input said playback user input during a predetermined first time interval and to control said speech generating means to generate the speech message upon detection of input of said playback user input during said first time interval,
to control said prompting means to provide a second prompt for a user to input said confirming user input during a predetermined third time interval and to control said speech generating means to generate a further speech message upon detection of input of said confirming user input during said third time interval,
to control said speech generating means to generate a counseling speech message upon detection of said counseling user input.

20. A health care compliance assistance system according to claim 19, wherein said prompting means comprises speech prompt generating means for generating a speech prompt message to prompt the user to input said predetermined one of said user inputs.

21. A health care compliance assistance system according to claim 19, wherein said programmed control means is programmed to repeat a most recently played speech message upon user repetition of input of said playback user input.

22. A health care compliance assistance system according to claim 21, wherein said programmed control means is further programmed to reduce power dissipation in said user device by limiting a number of repetitions of any speech message within a predetermined time interval.

23. A health care compliance assistance system according to claim 19, wherein said programmed control means is programmed to repeat the counseling speech message upon user repetition of input of said counseling user input.

24. A health care compliance assistance system according to claim 23, wherein said programmed control means is further programmed to reduce power dissipation in said user device by limiting a number of repetitions of the counseling speech message within a predetermined time interval.

25. A health care compliance assistance system according to claim 19, wherein said programmed control means is further programmed to respond to a number of user requested repetitions in excess of a predetermined threshold by controlling said speech generating means to append, to a next message to be generated thereby, a predetermined speech message indicative of excessive repetitions.

26. A health care compliance assistance system according to claim 19, wherein said programmed control means is programmed to maintain a database file identifying user compliance and non-compliance with a health care regimen, said programmed control means incrementing a count of missed opportunities to respond to said first prompt upon failure of a user to provide said playback user input during said first time interval, and incrementing a count of missed opportunities to respond to said second prompt upon failure of a user to provide said confirming user input during said third time interval.

27. A health care compliance assistance system according to claim 19, wherein said programmed control means is programmed to maintain a database file identifying a need for refilling a prescription corresponding to a specific medication regimen included in said user file by counting a number of times a user provides said confirming user input in response to said second prompt, said programmed control means programmed for calculating a difference between a predetermined number of doses in the prescription and the number of confirming user inputs provided in response to said second prompt, and for controlling said speech generating means to generate a refill speech message directing the user to refill the prescription when said difference is less than a predetermined value.

28. A health care compliance assistance system according to claim 26, wherein said programmed control means is further programmed for incrementing a count of missed opportunities to respond to a third prompt upon failure of a user to provide said confirming user input during a re-established third time interval.

29. A health care compliance assistance system according to claim 19, wherein said programmed control means is further programmed to maintain a database file identifying user operation of said user device and for incrementing a count of repetitions of said playback user input and of said counseling user input.

30. A health care compliance assistance system according to claim 19, wherein said programmed control means is further programmed to repeat a speech message in response to a user repeat-requesting input, and to reduce power dissipation in said user device by limiting a number of repetitions of any speech message within a predetermined time interval.

31. A health care compliance assistance system according to claim 30, wherein said user repeat-requesting input comprises one of said at least three interactive user inputs.

32. A health care compliance assistance system according to claim 30, wherein said user repeat-requesting input comprises a user input other than said at least three interactive user inputs.

33. A health care compliance assistance system comprising:
a host system, including:
input means for inputting speech data, user data and medication regimen data;
host storage means for storing said speech data, said user data and said medication regimen data;
programmed means responsive to said medication regimen data for generating a user file including speech data and scheduling times for generating a speech message corresponding to said medication regimen data; and transfer means;

a user device including:

user device storage means for storing said user file including said speech data transferred to said user device by said transfer means;

speech generating means for generating the speech message corresponding to the speech data stored in said user device storage means;

programmed control means for controlling said speech generating means to generate speech messages interactively with and responsive to a user;

user input means, and monitor connecting means for connection to a health monitoring device and for transmitting health monitor data to said programmed control means for storage in said user file;

said programmed control means programmed for responding to operation of a first of said user input means by controlling said speech generating means to generate a speech message directing the user to use the health monitoring device, and for responding to operation of a second of said user input means by analyzing the health monitor data transmitted thereto and by controlling said speech generating means to generate a speech message responsive to results of the analysis of the health monitor data, said programmed control means being further programmed to repeat a speech message in response to a user repeat-requesting input, and to reduce power dissipation in said user device by limiting a number of repetitions of any speech message within a predetermined time interval.

34. A health care compliance assistance system, comprising:

a host system, including host storage means for storing compressed speech data and user file data; and a user device receiving user file data and said compressed speech data from said host system for accessing selected compressed speech data corresponding to a selected speech message and for generating said selected speech message, including:

decompression means for decompressing said selected compressed speech data and providing decompressed speech data;

speech generating means for generating said selected speech message corresponding to the decompressed speech data;

programmed control means programmed for executing a program for comparing a current time with a predetermined time preset in the user file data received from said host system and, upon detecting a match therebetween, for controlling a user prompting means to generate a prompt, for initiating a time count and upon detection of a user response within a predetermined time interval, controlling said speech generating means to generate said selected speech message, thereby controlling said speech generating means to generate speech messages interactively with and responsive to a user.

35. A health care compliance assistance system according to claim 24, wherein said selected speech message comprises a plurality of speech phrases and said host storage means stores compressed speech phrase data, said user device accessing said selected compressed speech data corresponding to a plurality of phrases forming said selected speech message, said decompression means comprises means for decompressing said compressed speech phrase data;

said programmed control means further programmed for controlling said speech generating means to generate a first message segment including at least one speech phrase of said selected speech message and further programmed for, upon detection of a user response within a predetermined time interval following generation of said first message segment, controlling said speech generating means to generate a further message segment of said selected speech message.

36. A health care compliance assistance system according to claim 35, wherein said user device comprises user prompting means and user input means, and said programmed control means is programmed to control said speech generating means to play out a plurality of said message segments by:

providing a playback prompt to the user;

awaiting user activation of a playback input means;

controlling said speech generating means to play out one of said message segments if said playback input means is activated during a first time interval;

awaiting, during a third time interval, user activation of a confirming input means confirming said message segment; and generating another message segment upon detecting user activation of said confirming input means.

37. A health care compliance assistance system according to claim 36 wherein, upon detection of user failure to activate said playback input means during a second time interval corresponding to a maximum-effective-time (MET) for a medication associated with one of said speech messages, said programmed control means is further programmed to control said speech generating means to modify playback of a message segment associated with a subsequently scheduled speech message for said medication.

38. A health care compliance assistance system according to claim 36, wherein said user input means comprises counseling input means for providing unscheduled counseling messages to the user, said programmed control means programmed for responding to detection of activation of said counseling input means by controlling said speech generating means to generate a counseling message corresponding to a prescribed medication regimen included in said user file transferred from said host system to said user device.

39. A health care compliance assistance system according to claim 35, wherein said user device comprises a plurality of user prompting means and user input means, and said programmed control means is programmed to control said speech generating means to play out a particular message segment by:

providing an audible playback prompt to the user;

awaiting-user activation of a playback input means;

controlling said speech generating means to play out said particular message segment if said playback input means is activated during a first time interval; and controlling said speech generating means to repeat said particular message segment upon detection of a repeated activation of said playback input means.

40. A health care compliance assistance system according to claim 39, wherein said user device further comprises adaptive volume control means responsive to an absence of activation of said playback input means after expiration of said first time interval following said playback prompt and prior to expiration of a second predetermined time interval, said adaptive volume control means operating for controlling a predetermined one of said plurality of user prompting means to repeat said audible playback prompt at a higher volume level than the preceding audible playback prompt provided to the user.

41. A health care compliance assistance system according to claim 39, wherein said programmed control means is programmed to conserve power by limiting a number of repetitions of said speech message.

42. A health care compliance assistance system according to claim 35, wherein said host system comprises input means for inputting user profile data, and host storage means for storing said user profile data, and said user file transferred from said host system to said user device includes a prescribed health care regimen, said programmed control means being programmed to control said speech generating means to generate speech messages for playback at times established in accordance with said user profile data.

43. A health care compliance assistance system according to claim 34, further comprising:

remote satellite means, separate from said user device, and transmitting means for transmitting a signal from said user device to said remote satellite means;

said remote satellite means comprising:

receiving means for receiving the signal transmitted by said transmitting means, and prompt means controlled by said receiving means for outputting at said remote satellite means a preliminary prompting reminder to the user in response to transmission of said signal by said transmitting means of said user device to remind the user to provide a user response to said programmed control means for controlling said speech generating means to generate said selected speech message.

44. A health care compliance assistance system according to claim 35, wherein said user device comprises user input means, and monitor connecting means for connection to a health monitoring device and for transmitting health monitor data to said programmed control means for storage in said user file;

said programmed control means programmed for responding to operation of a first of said user input means by controlling said speech generating means to generate a first speech message directing the user to use the health monitoring device, and for responding to operation of a second of said user input means by analyzing said health monitor data transmitted thereto and by controlling said speech generating means to generate a second speech message responsive to results of the analysis of the health monitor data.

45. A health care compliance assistance system, comprising:

a host system, including:
input means for inputting speech data, user data and medication regimen data;
host storage means for storing said speech data, said user data and said medication regimen data;
programmed means responsive to said medication regimen data for generating a user file including speech data and scheduling times to be used in generating a speech message corresponding to said medication regimen data; and
transfer means;

a user device including:
user device storage means for storing said user file including speech data transferred to said user device by said transfer means;
speech generating means for generating the speech message corresponding to the speech data stored in said user device storage means; and
programmed control means for controlling said speech generating means to generate speech messages interactively with and responsive to a user, wherein said programmed control means is programmed to establish a time interval having a predetermined duration, after controlling said speech generating means to generate a speech message, and to await an interactive user confirmation input within said time interval, prior to controlling said speech generating means to generate a next speech message, to repeat a speech message in response to a user repeat-requesting input, and to reduce power dissipation in said user device by limiting a number of repetitions of any speech message within a predetermined time interval.

46. A health care compliance assistance system, comprising a host system and a user device;

said host system including:
input means for inputting speech data, user data and medication regimen data;
programmed means for generating a user file for transmission to the user device, said user file including said speech data, scheduling times, said medication regimen data, speech portion identifiers, and instructions for assembling a speech message;
host storage means for storing said speech data, said user data, said medication regimen data and said instructions for assembling a speech message; and
transfer means for transferring said user file to said user device;

said user device including:
user device storage means for storing said user file transferred by said transfer means, previously stored speech data, said speech portion identifiers, and said instructions for assembling a speech message;
programmed control means for assembling the speech message from the stored speech data in accordance with said instructions for assembling a speech message; said programmed control means controlling said speech generating means to generate speech messages interactively with and responsive to a user; and
speech generating means for generating the speech message assembled by said programmed control means of said user device, said programmed control means being programmed to repeat a speech message generated by said speech generating means in response to a user repeat-requesting input, and to reduce power dissipation in said user device by limiting a number of repetitions of any speech message within a predetermined time interval.

47. A health care compliance assistance system comprising:

a host system, including:
input means for inputting speech data, user data and medication regimen data, said user data including a user time schedule of an activity of an individual user;

host storage means for storing said speech data, said user data and said medication regimen data;

programmed means responsive to said medication regimen data for generating for the individual user a user file including scheduling times for generating a speech message corresponding to said medication regimen data and based on said user time schedule of the individual user; and transfer means;

a user device including:

user device storage means for storing speech data and said user file transferred to said user device by said transfer means;

speech generating means for generating the speech message corresponding to the speech data stored in said user device storage means; and programmed control means for controlling said speech generating means to generate speech messages interactively with and responsive to a user, wherein said user device further comprises:

means for entering at least three interactive user inputs, including a playback user input requesting playback of a scheduled speech message, a confirming user input for confirming receipt of the speech message, and a counseling user input requesting playback of an unscheduled counseling message;

prompting means for generating a prompt to inform the user of a requirement for inputting a predetermined one of said playback and confirming user inputs, and said programmed control means is programmed to control said prompting means to provide a first prompt for a user to input said playback user input during a predetermined first time interval and to control said speech generating means to generate the speech message upon detection of input of said playback user input during said first time interval, to control said prompting means to provide a second prompt for a user to input said confirming user input during a predetermined third time interval and to control said speech generating means to generate a further speech message upon detection of input of said confirming user input during said third time interval, and to control said speech generating means to generate a counseling speech message upon detection of said counseling user input.

* * * * *